US008722884B2

(12) United States Patent
Kath et al.

(10) Patent No.: US 8,722,884 B2
(45) Date of Patent: May 13, 2014

(54) PYRIMIDINE DERIVATIVES FOR THE TREATMENT OF ABNORMAL CELL GROWTH

(75) Inventors: John Charles Kath, La Mesa, CA (US); Michael Joseph Luzzio, Noank, CT (US); Susan La Greca, Old Lyme, CT (US); Nandini Chaturbhai Patel, Providence, RI (US)

(73) Assignee: Verastem, Inc., Cambridge, MA (US)

( * ) Notice: Subject to any disclaimer, the term of this patent is extended or adjusted under 35 U.S.C. 154(b) by 735 days.

(21) Appl. No.: 12/095,716

(22) PCT Filed: Nov. 20, 2006

(86) PCT No.: PCT/IB2006/003349
§ 371 (c)(1),
(2), (4) Date: Oct. 18, 2010

(87) PCT Pub. No.: WO2007/063384
PCT Pub. Date: Jun. 7, 2007

(65) Prior Publication Data
US 2011/0033441 A1   Feb. 10, 2011

Related U.S. Application Data

(60) Provisional application No. 60/741,252, filed on Dec. 1, 2005.

(51) Int. Cl.
*C07D 403/12* (2006.01)
*A61K 31/505* (2006.01)

(52) U.S. Cl.
USPC .................................. 544/324; 514/275

(58) Field of Classification Search
USPC .......................... 544/324; 514/275
See application file for complete search history.

(56) References Cited

U.S. PATENT DOCUMENTS

| | | | |
|---|---|---|---|
| 4,344,948 A * | 8/1982 | Takai et al. .................... | 514/300 |
| 5,602,250 A * | 2/1997 | Broom et al. ................. | 540/310 |
| 5,795,909 A * | 8/1998 | Shashoua et al. ............. | 514/449 |
| 6,063,927 A * | 5/2000 | Craig et al. ................... | 546/197 |
| 6,531,139 B1 * | 3/2003 | Gao et al. ....................... | 424/400 |
| 6,645,972 B2 * | 11/2003 | Jolivet et al. .................. | 514/274 |
| 2003/0212100 A1 * | 11/2003 | Tsunoda et al. .............. | 514/311 |
| 2004/0220177 A1 | 11/2004 | Kath et al. | |
| 2005/0256111 A1 | 11/2005 | Kath et al. | |
| 2005/0256125 A1 | 11/2005 | Kath et al. | |
| 2005/0256144 A1 | 11/2005 | Kath et al. | |
| 2005/0256145 A1 | 11/2005 | Kath et al. | |

FOREIGN PATENT DOCUMENTS

WO    WO 2004/056807    7/2004

OTHER PUBLICATIONS

Stahl et al., eds., Handbook of pharmaceutical salts. Properties, selection and use (Wiley-VCH, 2008), pp. 265-327.*
Serajuddin, Advanced Drug Delivery Reviews 59 (2007) 603-616.*
Liu, Rong, ed., Water-Insoluble Drug Formulation (CRC Press, 2008) Chapter 15 pp. 417-435.*
Bastin et al., Organic Process Research & Development 2000, 4, 427-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Gould, International J. of Therapeutics 33, pp. 201-213 & 217 (1986).*
Swarbrick et al., eds. Encyclopedia of Pharmaceutical Technology 13 (Marcel Dekker, NY 1996) pp. 453-499.*
Simone, Oncology: Introduction, Cecil Textbook of Medicine, 20th Edition, vol. 1, pp. 1004-1010, 1996.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
S.L. Morissette et al., Advanced Drug Delivery Reviews, 56,275-300 (2004).*
S.R. Vippagunta et al., Advanced Drug Delivery Reviews, 48, 3-26 (2001).*
Bastin, Richard J. et al., "Salt Selection and Optimisation Procedures for Pharmaceutical New Chemical Entities", Organic Process Research & Dev., 2000, 427-435, vol. 4, No. 5.
Desrosiers, P., et al., "High throughput screening techniques for pre-formulation: Salt selection and polymorph studies", ACTA Cryst., 2002, 1, vol. A58 (Supplement), C9.
Written Opinion of International Search Authority for PCT/IB2006/003349 dated Jul. 25, 2007.
International Search Report of PCT/IB2006/003349 dated Jul. 25, 2007.
International Preliminary Report of PCT/IB2006/003349 dated Jun. 3, 2008.

* cited by examiner

*Primary Examiner* — Deepak Rao
(74) *Attorney, Agent, or Firm* — Lando & Anastasi LLP

(57) ABSTRACT

The present invention relates to salts, solvates and substoichiometric solvates of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide. The invention also provides pharmaceutical compositions comprising such complexes, as well as methods of treating abnormal cell growth by administering the complexes of the invention.

5 Claims, 19 Drawing Sheets

PYRIMIDINE DERIVATIVES FOR THE TREATMENT OF ABNORMAL CELL GROWTH

CROSS-REFERENCE TO RELATED APPLICATIONS

This application is a §371 filing of PCT/IB2006/003349 filed Nov. 20, 2006, which claims the benefit of priority to U.S. Provisional Application No. 60/741,252 filed Dec. 1, 2005; the entire contents of which are incorporated herein by reference.

FIELD OF THE INVENTION

This invention relates to novel salts, solvates, and substoichiometric solvates of pyrimidine derivatives that are useful in the treatment of abnormal cell growth, such as cancer, in mammals. More particularly, the invention relates to besylate, mesylate, tosylate, and hydrochloride salts of 2,4-diamino-substituted pyrimidines that are useful in the treatment of abnormal cell growth in mammals, especially humans, and to pharmaceutical compositions containing such complexes.

BACKGROUND

The present invention relates to complexes of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide having Formula I:

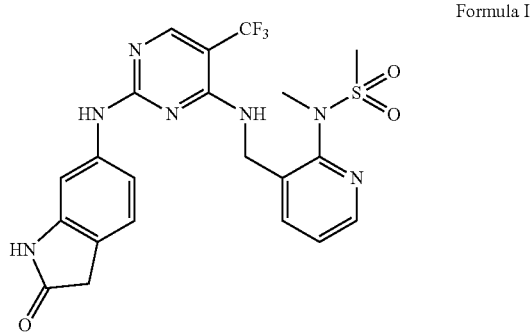 [SMILES: CN(c1ncccc1CNc1nc(Nc2ccc3c(c2)NC(=O)C3)ncc1C(F)(F)F)S(C)(=O)=O]

Formula I

Formula I in its amorphous free base form is described in co-pending U.S. Ser. No. 11/127,809, filed May 12, 2005, the disclosure of which is hereby incorporated herein by reference in its entirety. The foregoing application is assigned in common with the present application. The amorphous free base of Formula I is useful in the treatment of hyperproliferative diseases, such as cancers.

The present invention relates to methods of making salts and solvates of Formula I, and more particularly, besylate, mesylate, tosylate, and hydrochloride salts of Formula I, as well as pharmaceutical compositions containing these various forms of Formula I (referred to herein as complexes of Formula I). The complexes of the present invention are useful in the treatment of hyperproliferative diseases, such as cancers, in mammals, especially humans. The invention also relates to methods of administering the complexes of Formula I to treat hyperproliferative diseases.

SUMMARY

Therefore, the present invention provides various complexes of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide.

In one embodiment, the invention relates to pharmaceutically acceptable salts of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide. In particular, the invention provides the besylate salt of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide; the mesylate salt of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide; the tosylate salt of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide; and the HCl salt of N-[3-[[[2-[(2,3-dihydro-2-oxo-1H-indol-5-yl)amino]-5 (trifluoromethyl)-4-pyrimidinyl]amino]methyl]-2-pyridinyl]-N-methylmethanesulfonamide.

In one embodiment of the present invention, the various salts of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide are substoichiometric solvates. For example, the substoichiometric solvates may comprise ethanol.

In a further embodiment, the invention provides complexes that exhibit the X-ray powder diffraction spectrum substantially the same as the X-ray powder diffraction spectrum shown in FIGS. 1(e), 2(b), 3(b), and 4(d).

The invention also provides a substoichiometric solvate of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide. In one embodiment, the solvate comprises a solvent selected from the group consisting of water, an alcohol, a polar organic solvent, and combinations thereof. In a further embodiment, the solvent is selected from the group consisting of water, ethanol, and combinations thereof. In another embodiment, the solvate comprises ethanol in a range of about 0.1 to about 3 mol %, and preferably in a range of about 0.4 to about 2% mol.

The invention also provides a pharmaceutical composition comprising an amount of a salt or solvate as described herein that is effective in treating abnormal cell growth, and a pharmaceutically acceptable carrier or diluent.

The invention further provides a method for the treatment of abnormal cell growth in a mammal comprising administering to said mammal an amount of a salt or solvate as described herein that is effective in treating abnormal cell growth. In one embodiment, the abnormal cell growth is cancer, and in a further embodiment the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. Preferably, the invention provides a method for the treatment of cancer solid tumor in a mammal comprising administering to said mammal an amount of a salt or solvate as described above that is effective in treating said cancer solid tumor. Such solid tumors are selected from breast, lung, colon, brain, prostate, stomach, pancreatic, ovarian, skin (melanoma), endocrine, uterine, testicular, or bladder.

Finally, the invention also provides a method for the treatment of abnormal cell growth in a mammal which comprises administering to said mammal an amount of a salt or solvate as described herein that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

BRIEF DESCRIPTION OF THE FIGURES

FIG. 1(*b*) is a DSC scan of the monobesylate salt of Formula I.
FIG. 1(*c*) is a TGA of the monobesylate salt of Formula I.
FIG. 1(*d*) is a VTI moisture adsorption/desorption isotherm of monobesyltate salt of Formula I.
FIG. 1(*e*) is a PXRD of the monobesyltate salt of Formula I.
FIG. 2(*b*) is a PXRD of the monomesyltate salt of Formula I.
FIG. 2(*c*) is a DSC scan of the monomesylate salt of Formula I.
FIG. 2(*d*) is a VTI moisture adsorption/desorption isotherm of monomesyltate salt of Formula I.
FIG. 3(*b*) is a PXRD of the tosylate salt of Formula I.
FIG. 3(*c*) is a DSC scan of the tosylate salt of Formula I.
FIG. 3(*d*) is a VTI moisture adsorption/desorption isotherm of tosylate salt of Formula I.
FIG. 3(*e*) is a TGIR analysis of the tosylate salt of Formula I.
FIG. 4(*b*) is a PXRD of the HCl salt of Formula I.
FIG. 4(*c*) is a PXRD of the HCl salt of Formula I.
FIG. 4(*d*) is a DSC scan of the HCl salt of Formula I.
FIG. 4(*e*) is a VTI moisture adsorption/desorption isotherm of HCl salt of Formula I.

DETAILED DESCRIPTION

Figure 1A:
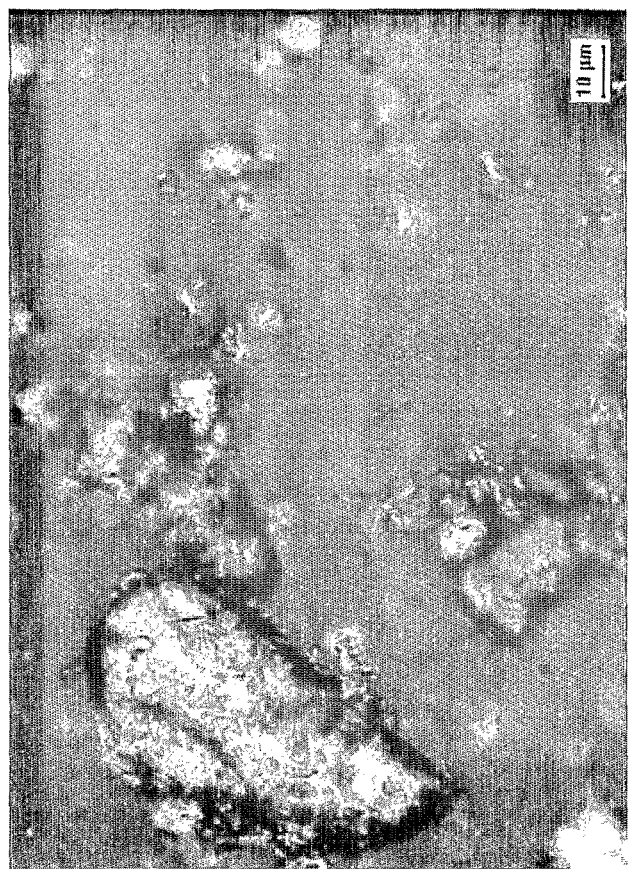
FIG. 1(*a*) is a polarized light micrograph of the monobesylate salt of Formula I.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. As used herein, each of the following terms has the meaning associated with it in this section. The articles "a" and "an" are used herein to refer to one or to more than one (i.e., to at least one) of the grammatical object of the article. By way of example, "an element" means one element or more than one element.

The present invention relates to salts and solvates of Formula I. The term "solvate" as used herein refers a compound consisting of an ion or molecule of solute combined with one or more solvent molecules, such that the "solvate" refers to an aggregate of solute and solvent. Alternatively, the present invention relates to "substoichiometric solvates" of Formula I in which less than one solvent molecule is combined with an ion or molecule of solute. The terms "solvate" and "substoichiometric solvate" do not necessarily require a fixed ratio of solute to solvent molecules. Suitable solvent molecules include water, alcohols and other polar organic solvents. Suitable alcohols include methanol, ethanol, n-propanol, isopropanol, n-butanol, isobutanol, and t-butanol. In a preferred embodiment, the solvent is water or ethanol. In more a preferred embodiment, the solvent is ethanol and approximately 0.1 to about 3 mol % ethanol is present in the solvate, more preferably about 0.4 to about 2 mol % ethanol is present in the solvate. Suitable alcohols also include polymerized alcohols such as polyalkylene glycols (e.g., polyethylene glycol, polypropylene glycol). If the solvent is water the solvate compounds or complexes formed by solvation with water are termed hydrates. In one embodiment, the solvates are crystalline. Solvates of Formula I can be prepared by crystallizing the compound of Formula I from a solvent in the presence of a molecule that is capable of donating and/or accepting a hydrogen bonding interaction to the compound of Formula I.

Salts of the present invention are prepared by contacting a free base of Formula I with a solvent. Suitable solvents include water, alcohols, other polar organic solvents, and combinations thereof. Methanol is a preferred solvent. Free base is reacted with a suitable acid such that Formula I forms a salt and preferably dissolves. Suitable acids can be added to the free base of Formula I with the solvent (i.e., dissolved in the solvent), such that the free base is solvated and protonated essentially simultaneously, or bases can be added after the free base has been contacted with solvent. In the latter scenario, bases can either be dissolved in a solvent, which can be either the solvent already contacting free base or a different solvent can be added as a neat solid or liquid, or a combination thereof. Evaporation of solvent can be followed by re-dissolving the salt in a suitable solvent for crystallization. Also, filtration followed by the addition of a seed crystal can be used as an alternate procedure to crystallize the salt. In each case, the suitable solvent or the seed crystal acts as a crystallization promoter for the salt. Depending on the solvent utilized, a salt may precipitate and/or crystallize independently of evaporation. Crystals of a salt can be filtered to remove bulk solvent.

In a preferred embodiment, the free base of Formula I is combined with a molar excess of a suitable acid in a suitable solvent. If the besylate salt of Formula I is sought, the free base is combined with a molar excess, e.g., up to 3 equivalents, preferably up to 2 equivalents, more preferably up to 1.5 equivalents, of benzenesulfonic acid. If the mesylate salt of Formula I is sought, the free base is combined with a molar excess, e.g., up to 3 equivalents, preferably up to 2 equivalents, more preferably up to 1.5 equivalents, of methanesulfonic acid. If the tosylate salt of Formula I is sought, the free base is combined with a molar excess, e.g., e.g., up to 3 equivalents, preferably up to 2 equivalents, more preferably up to 1.5 equivalents, of p-toluenesulfonic acid. Finally, if the hydrochloride, salt of Formula I is sought, the free base is combined with a molar excess, e.g., e.g., up to 3 equivalents, preferably up to 2 equivalents, more preferably up to 1.5 equivalents, of hydrochloric acid. This general procedure may be modified by the skilled artisan to prepare a variety of additional salts of Formula I, including but not limited to those that form non-toxic acid addition salts, e.g., salts containing pharmacologically acceptable anions, such as the hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, ethanesulfonate, p-toluenesulfonate and pamoate [i.e., 1,1'-methylene-bis-(2-hydroxy-3-naphthoate)] salts. The free base of Formula I may also form pharmaceutically acceptable salts with various amino acids, in addition to the acids mentioned above.

A salt of Formula I can be transformed into a second salt of Formula I by transmetallation or another process that replaces the cation of the first salt. In one example, a potassium salt of Formula I is prepared and is subsequently reacted with a second salt such as an alkaline earth metal halide (e.g., $MgBr_2$, $MgCl_2$, $CaCl_2$, $CaBr_2$), an alkaline earth metal sulfate or nitrate (e.g., $Mg(NO_3)_2$, $Mg(SO_4)_2$, $Ca(NO_3)_2$, $Ca(SO_4)_2$), or an alkaline earth metal salt of an organic acid (e.g. calcium formate, magnesium formate, calcium acetate, magnesium acetate, calcium propionate, magnesium propionate) to form an alkaline earth metal salt of Formula I.

Salts of Formula I can comprise solvate molecules in stoichiometric or substoichiometric amounts and can occur in a variety of solvation states which are also known as solvates. Different solvates of a salt of the present invention can be obtained by varying the method of preparation. Solvates typically have different solubilities, such that a more thermodynamically stable solvate is less soluble than a less thermodynamically stable solvate. Solvates can also differ in properties such as shelf-life, bioavailability, morphology, vapor pressure, density, color, and shock sensitivity. The complexes of the present invention exhibit enhanced physical properties in relation to the corresponding amorphous form, including but not limited to enhanced shelf-life, bioavailability, morphology, vapor pressure, density, color, and shock sensitivity. Suitable solvate molecules include water, alcohols, other polar organic solvents, and combinations thereof. Alcohols include methanol, ethanol, n-propanol, isopropanol, n-butanol, isobutanol, and t-butanol. Water is a preferred solvent. Solvate molecules can be removed from a crystalline salt, such that the salt is either a partial or complete desolvate. If the solvate molecule is water (forming a hydrate), then a desolvated salt is said to be a dehydrate. A salt with all water removed is anhydrous. Solvate molecules can be removed from a salt by methods such as heating, treating under vacuum or reduced pressure, blowing air over a salt, or a combination thereof.

A salt of the present invention, in one of the above-listed forms, can co-crystallize with one or more other substances. The other substance or substances can be, for example, a salt, a free acid, or a free base, and can interact with a salt through hydrogen bonds and other energetically-favorable means.

In another embodiment of the present invention, the salts of the present invention are substantially pure. A salt that is substantially pure can be greater than about 80% pure, greater than about 85% pure, greater than about 90% pure, greater than about 95% pure, greater than about 98% pure, or greater than about 99% pure. Purity of a salt can be measured with respect to the amount of salt (as opposed to unreacted neutral Formula I or base) or can be measured with respect to a specific solvate, polymorph, desolvate, hydrate, dehydrate, or anhydrous form of a salt.

Figure 1B:
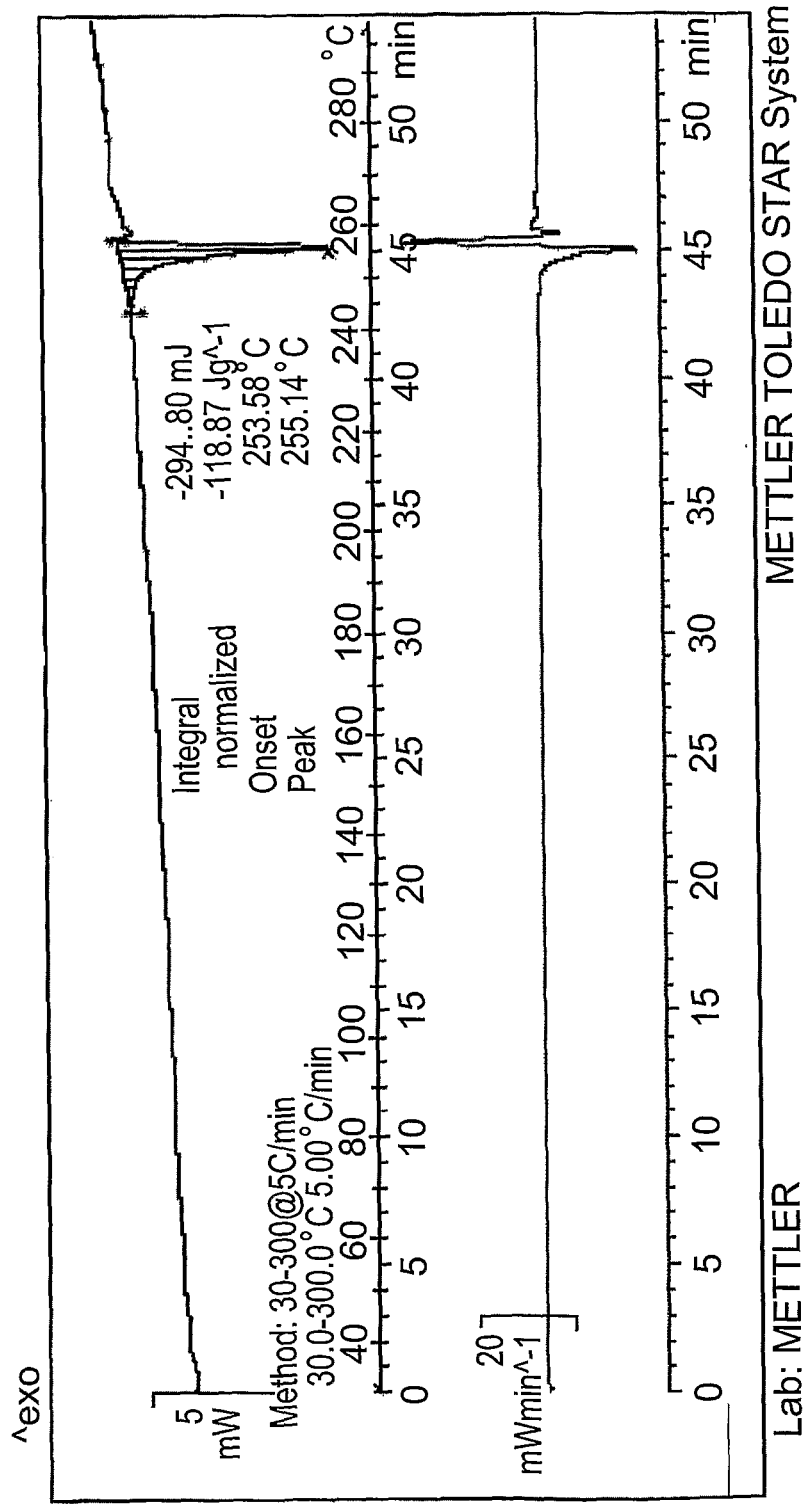
Figure 1C:
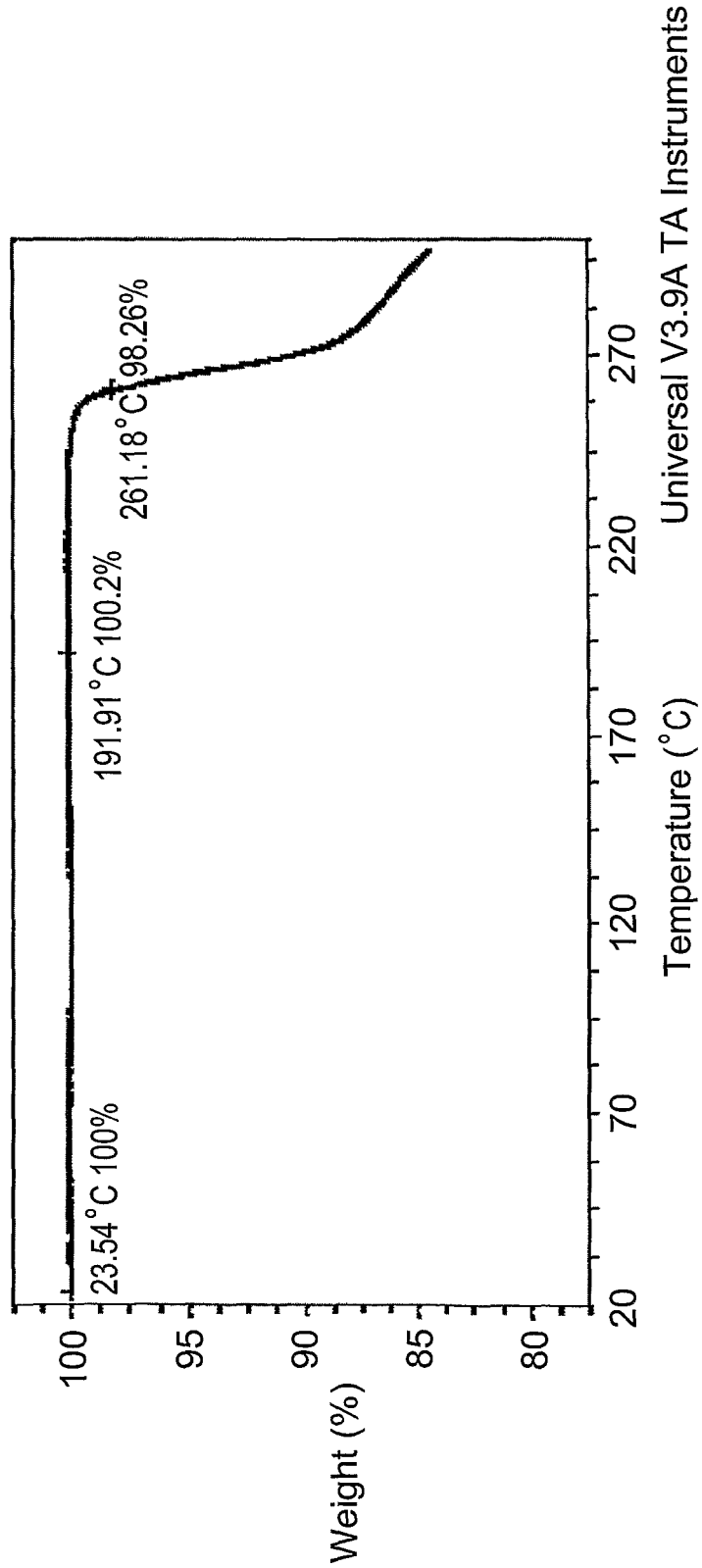
Figure 1D:
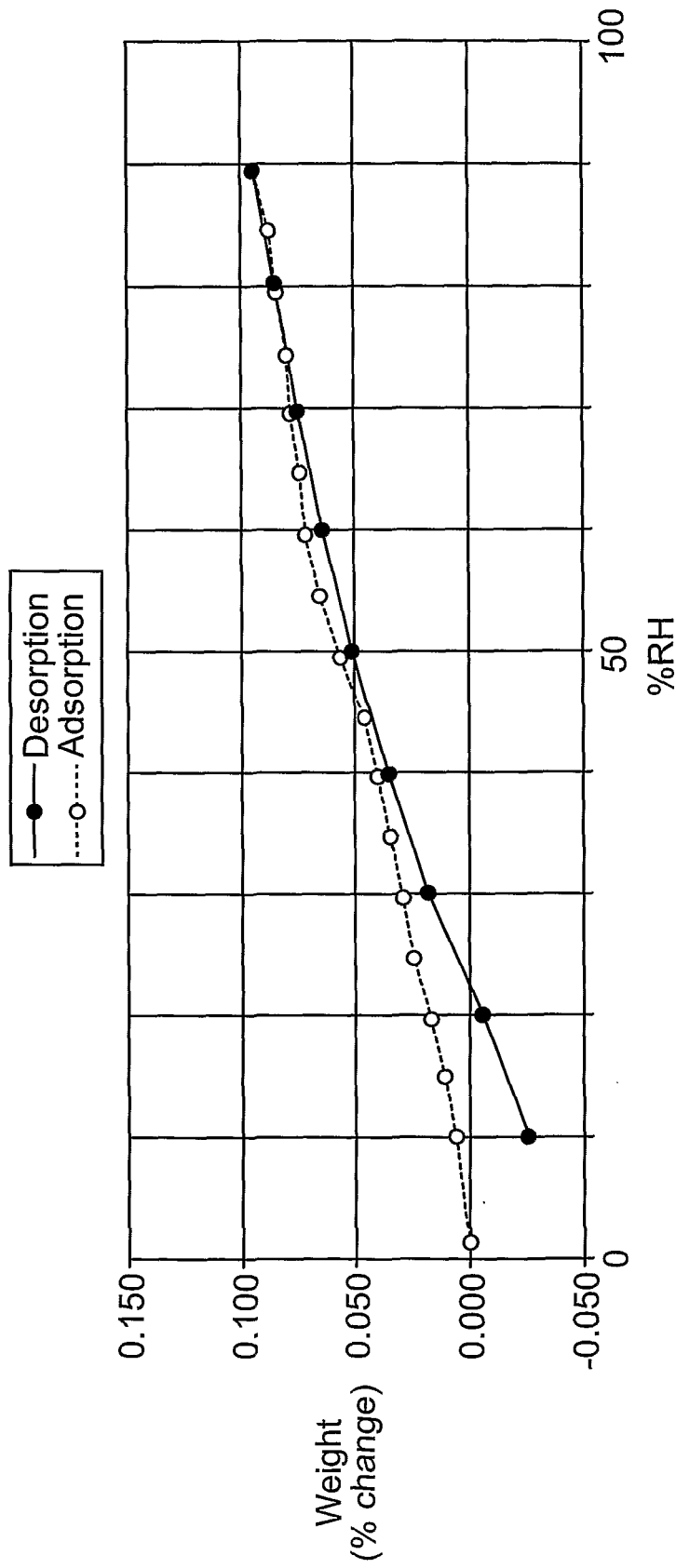
Figure 1E:
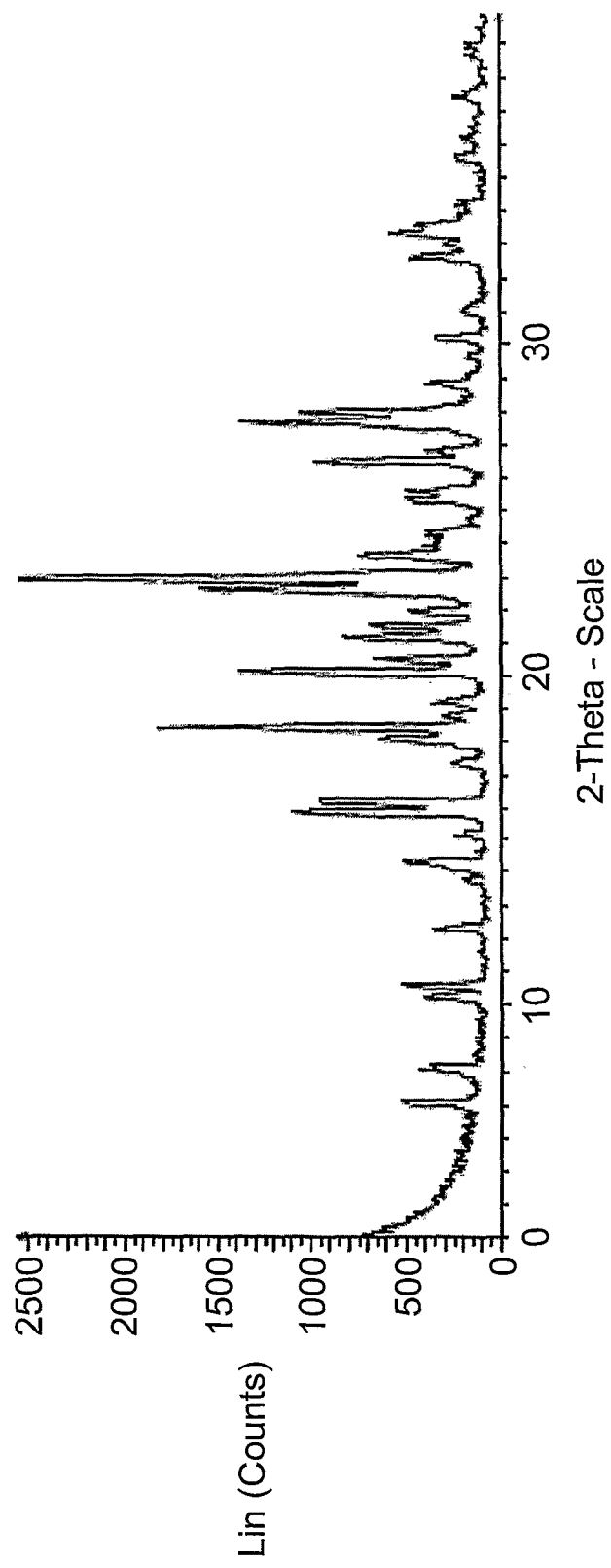
Figure 2A:
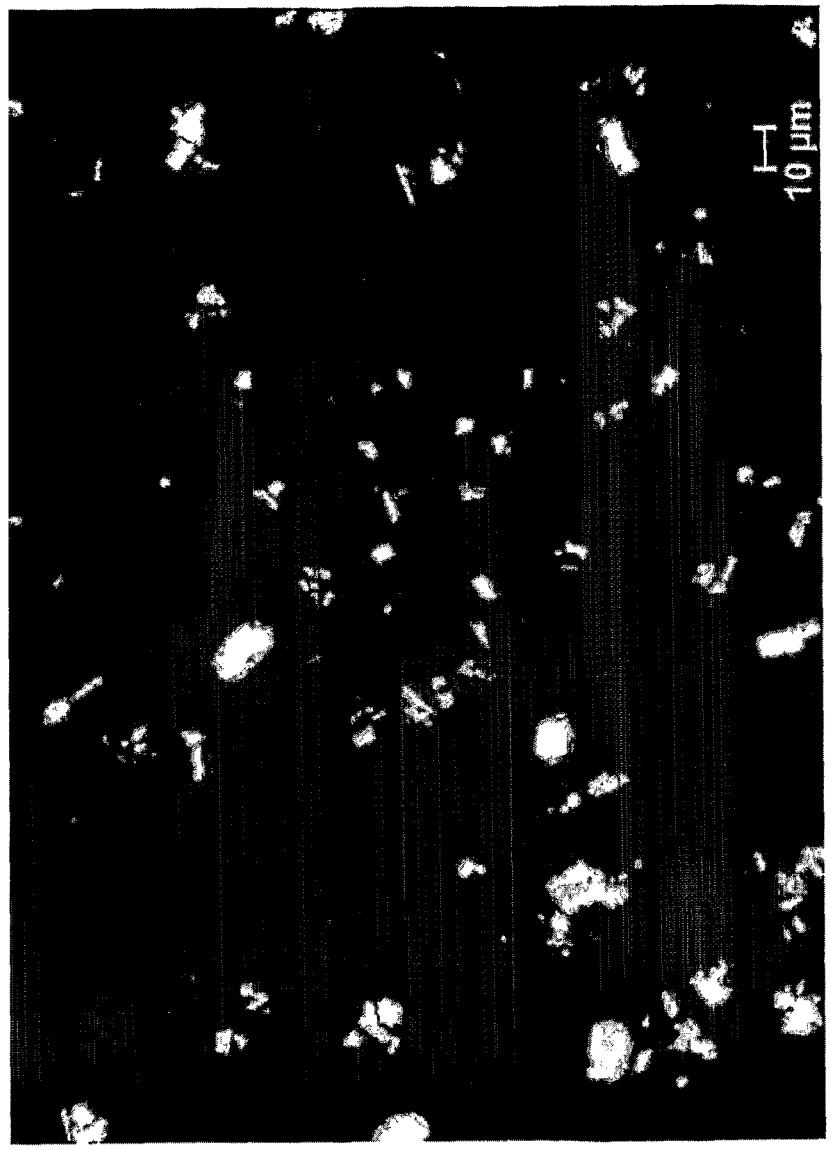
FIG. 2(*a*) is a polarized light micrograph of the monomesylate salt of Formula I.
Figure 2B:
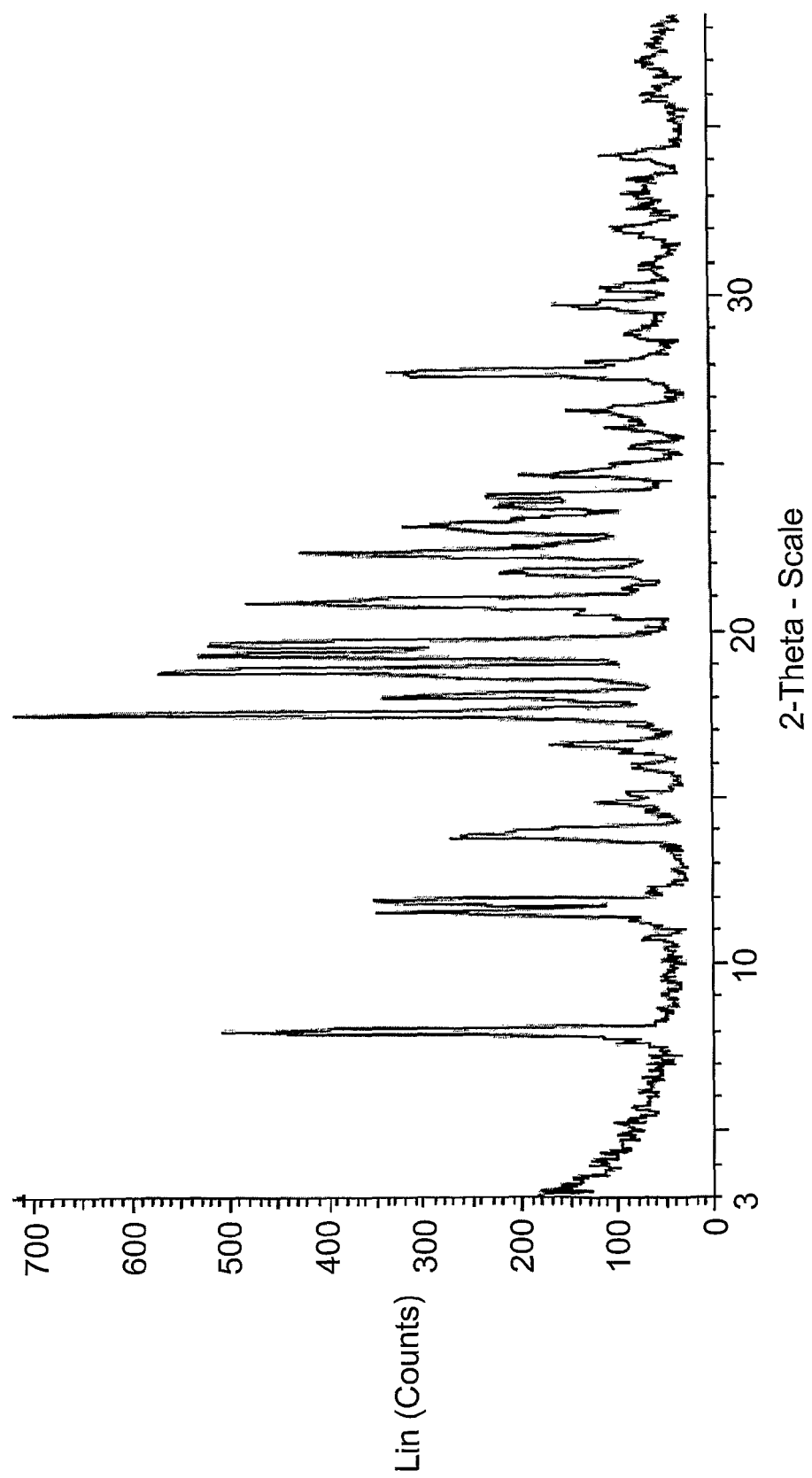
Figure 2C:
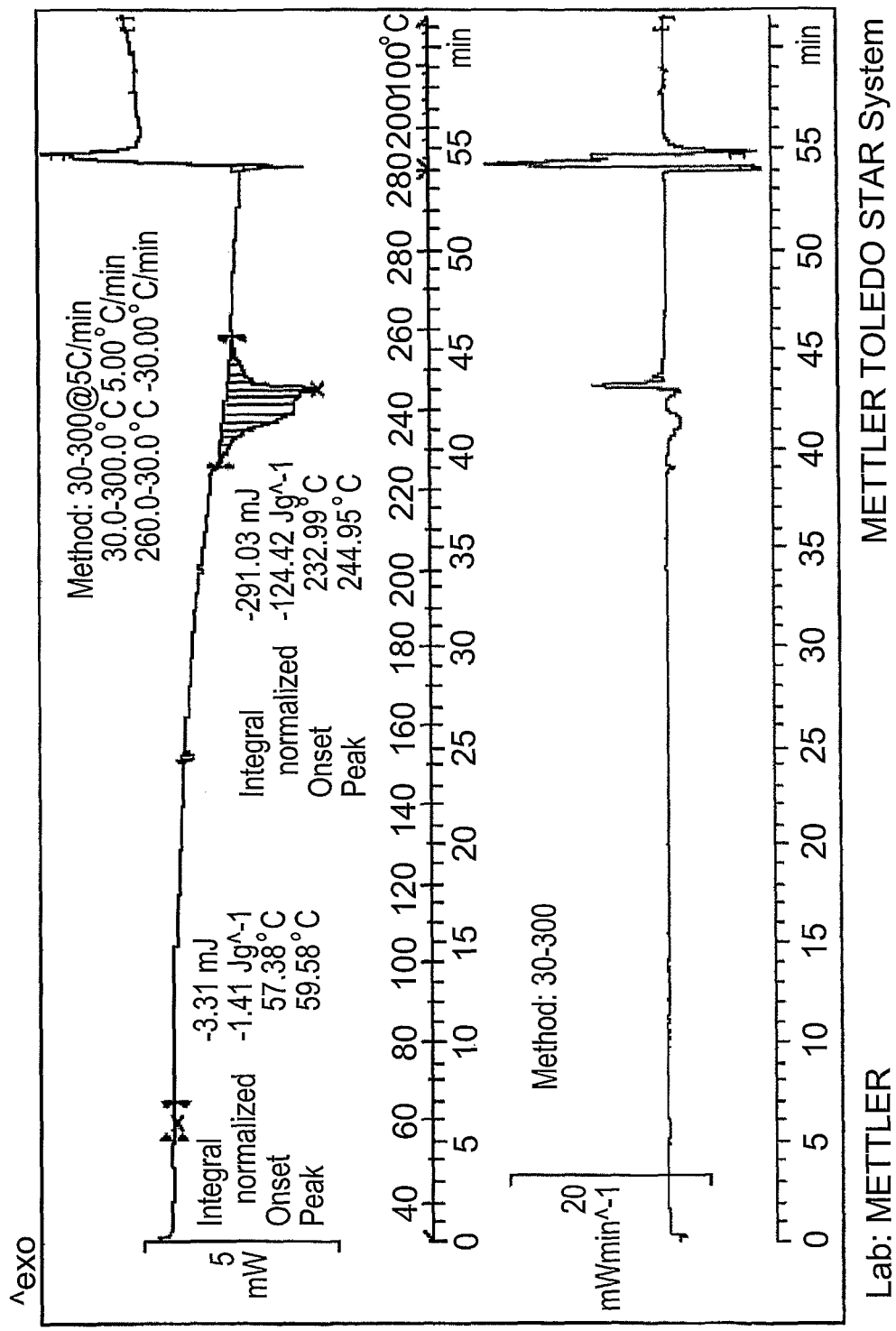
Figure 2D:
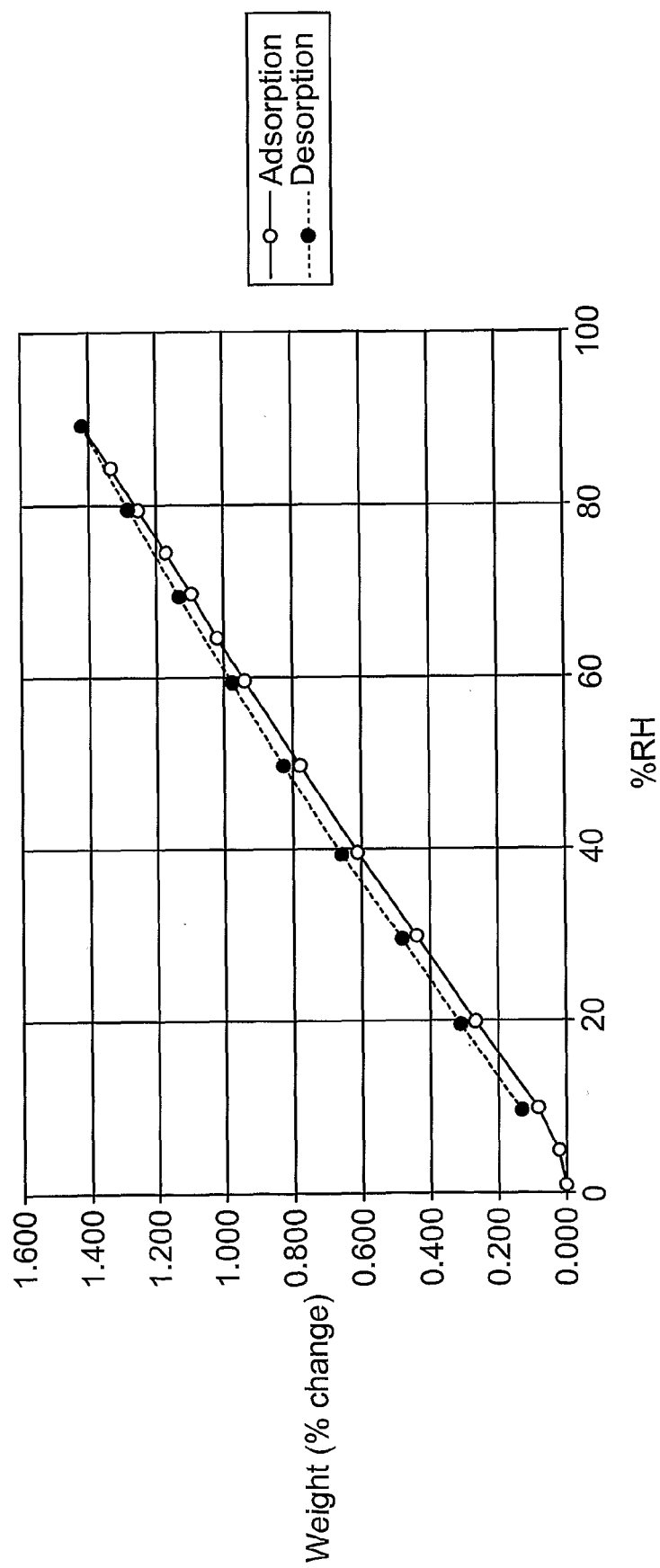
Figure 3A:
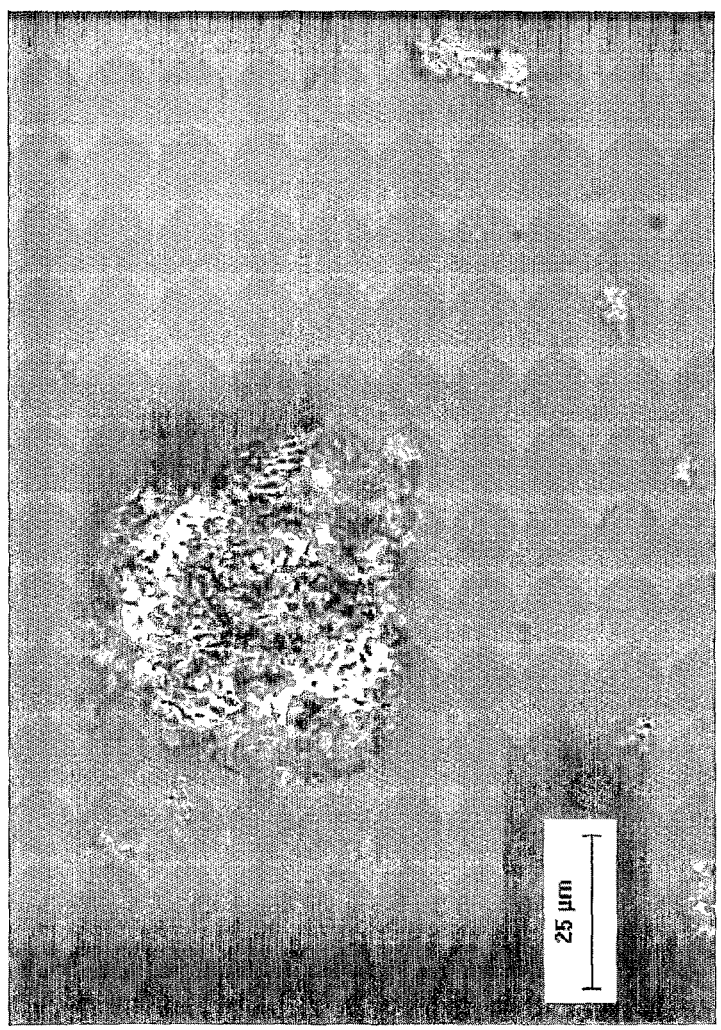
FIG. 3(*a*) is a polarized light micrograph of the tosylate salt of Formula I.
Figure 3B:
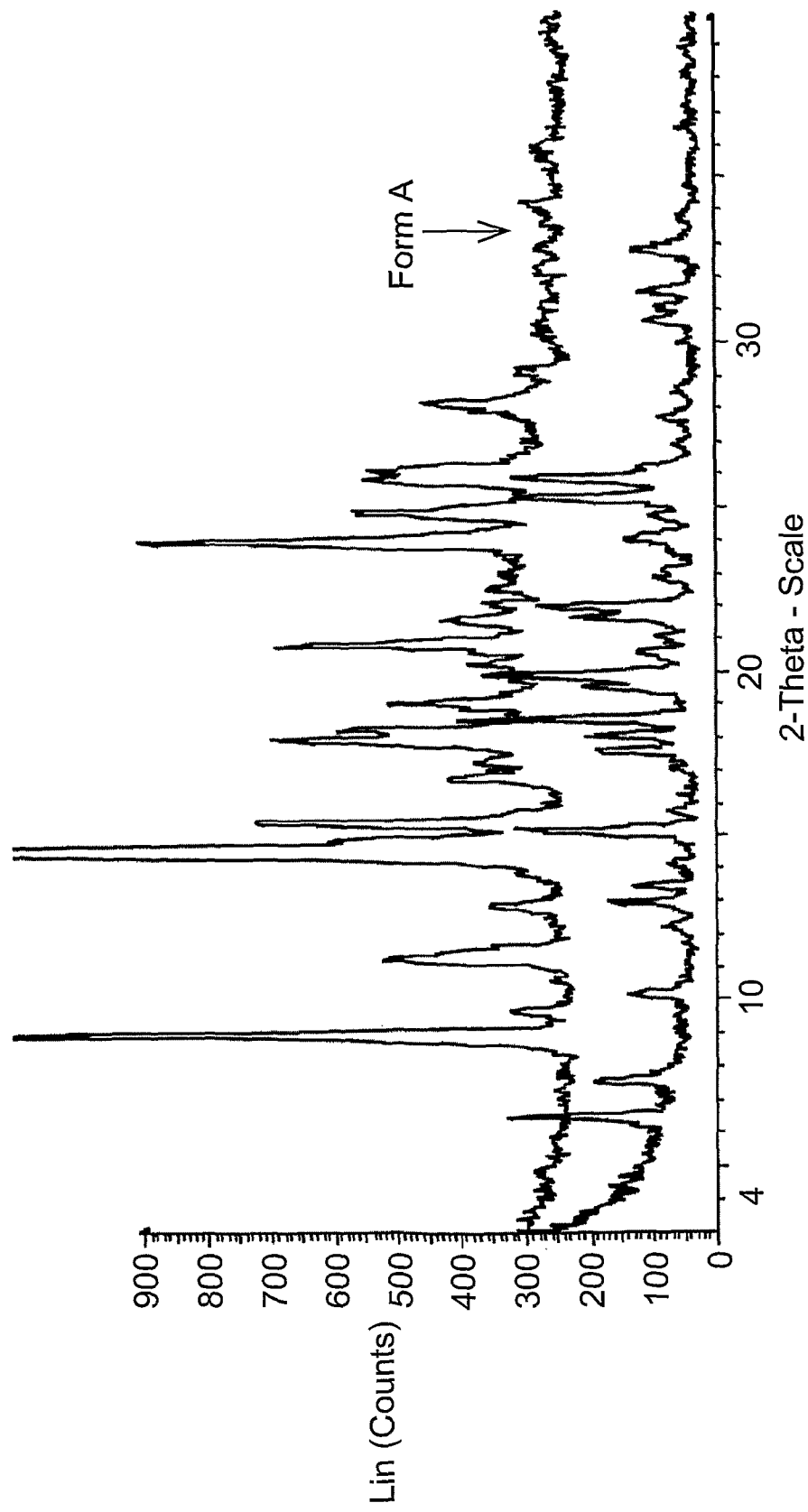
Figure 3C:
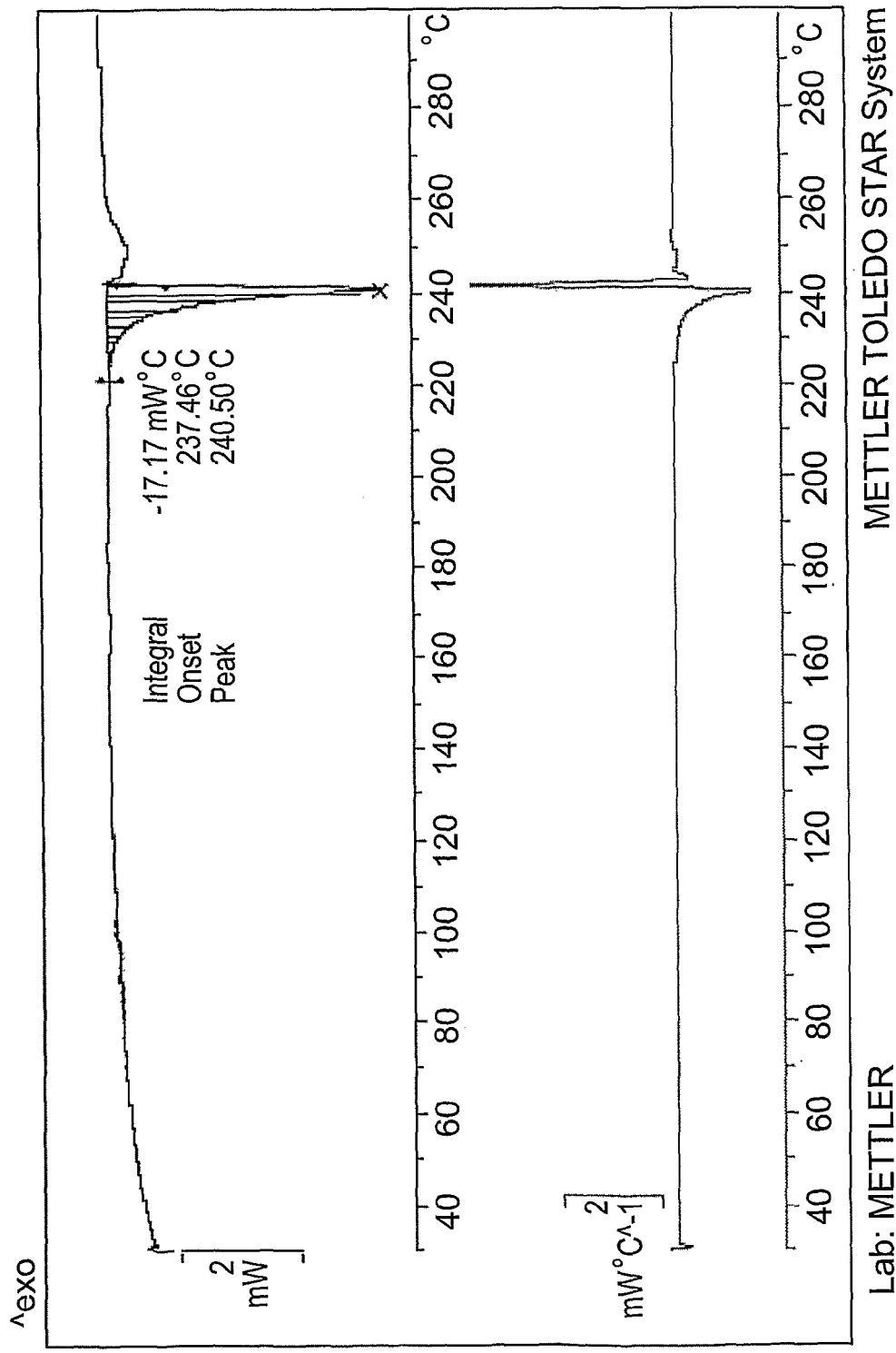
Figure 3D:
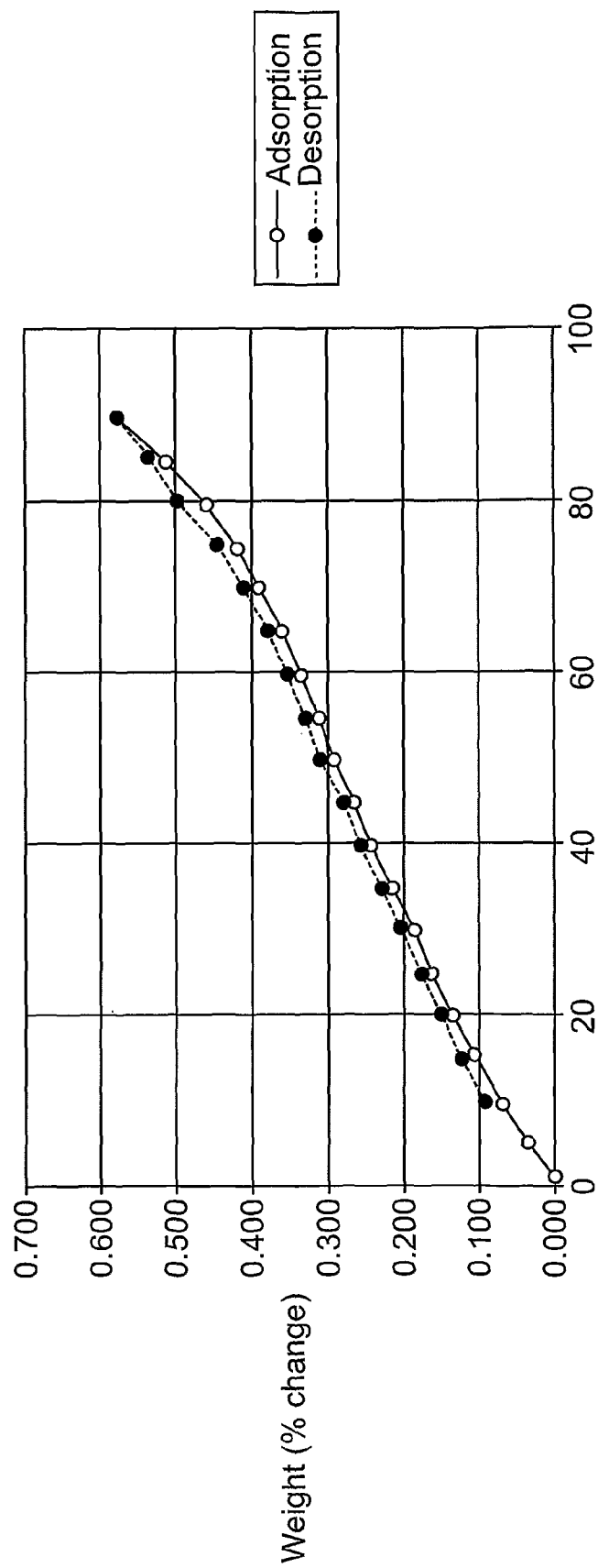
Figure 3E:
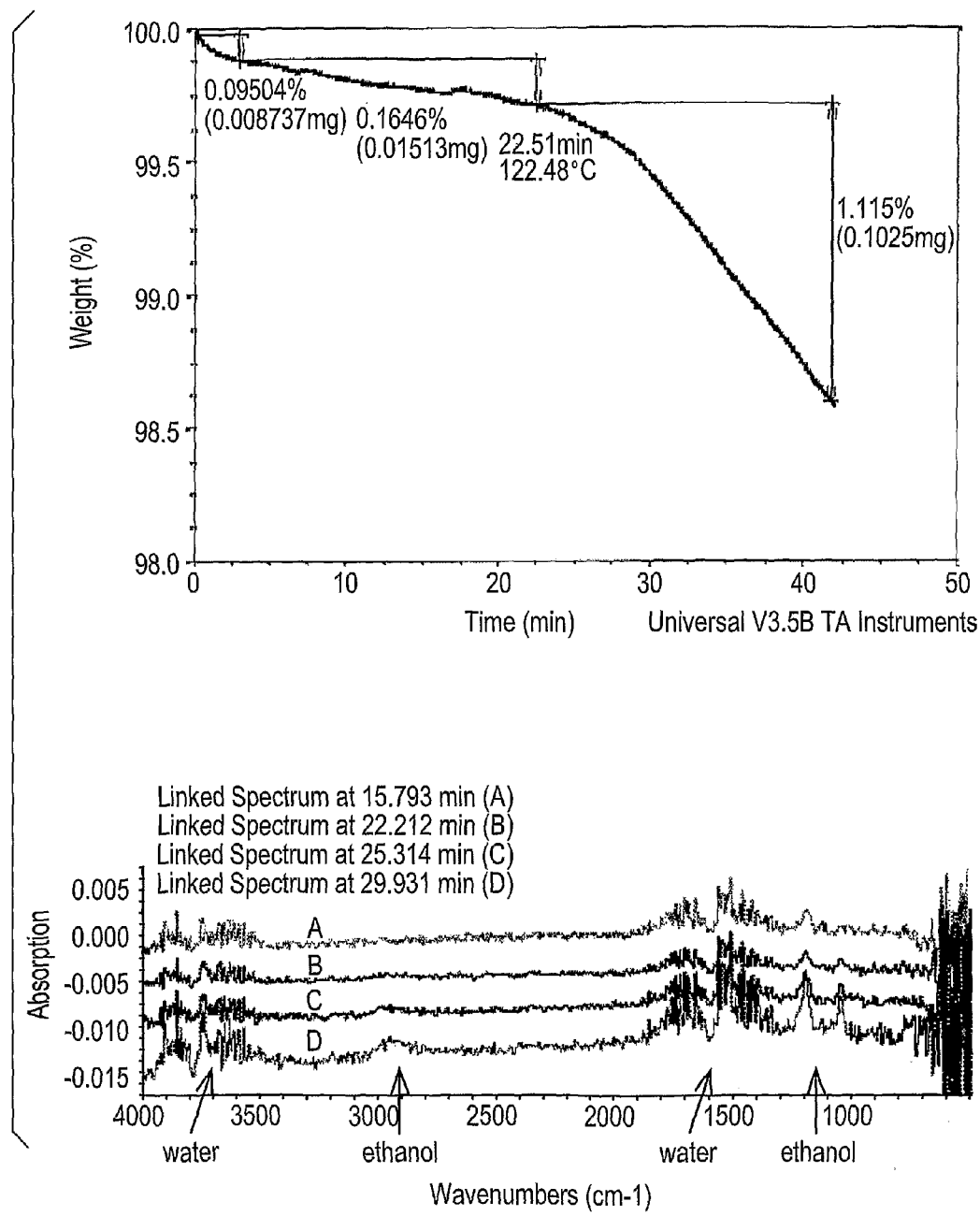
Figure 4A:
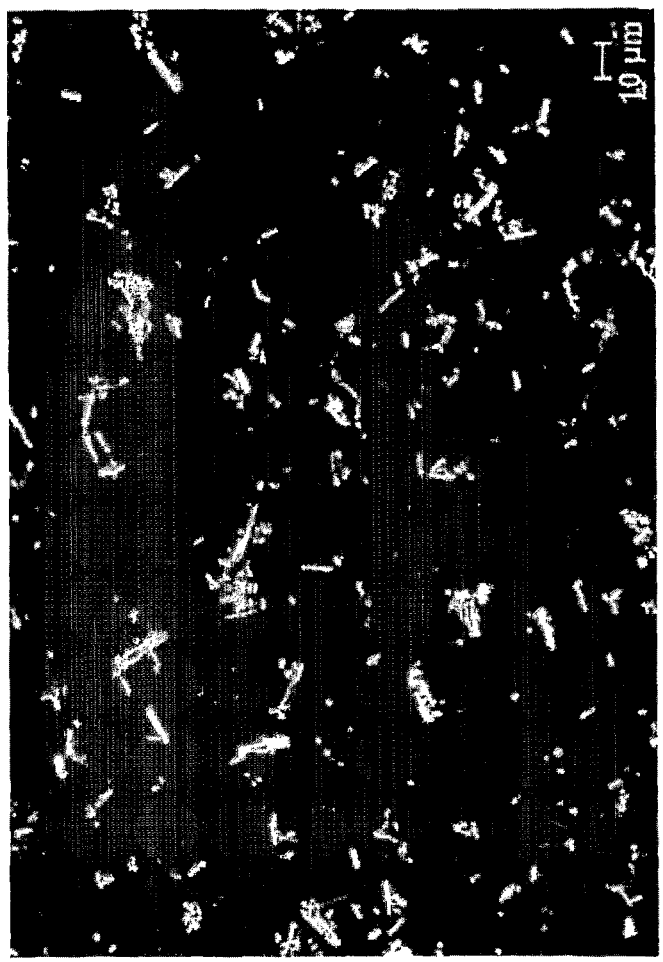
FIG. 4(*a*) is a polarized light micrograph of the HCl salt of Formula I.
Figure 4B:
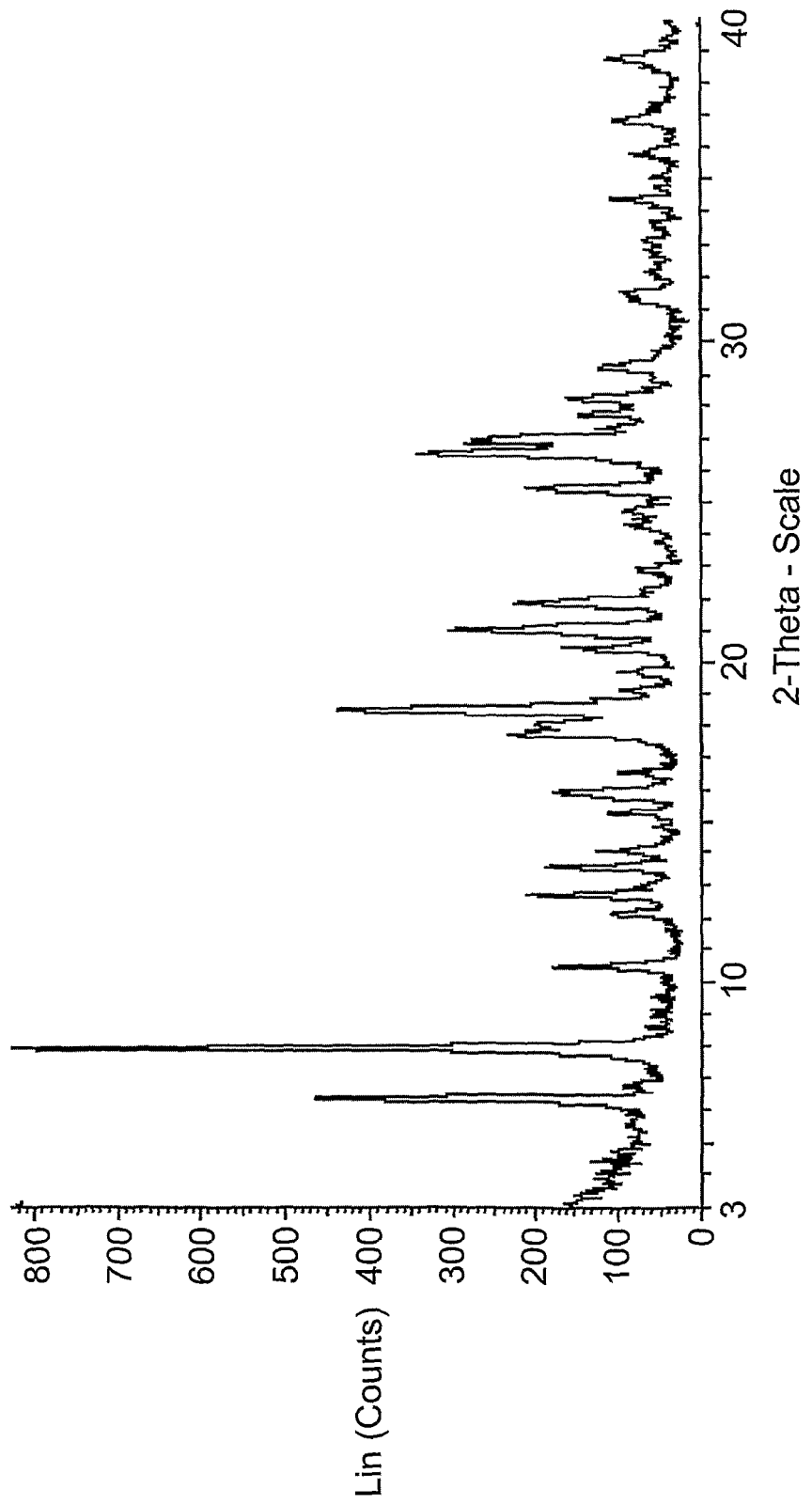
Figure 4C:
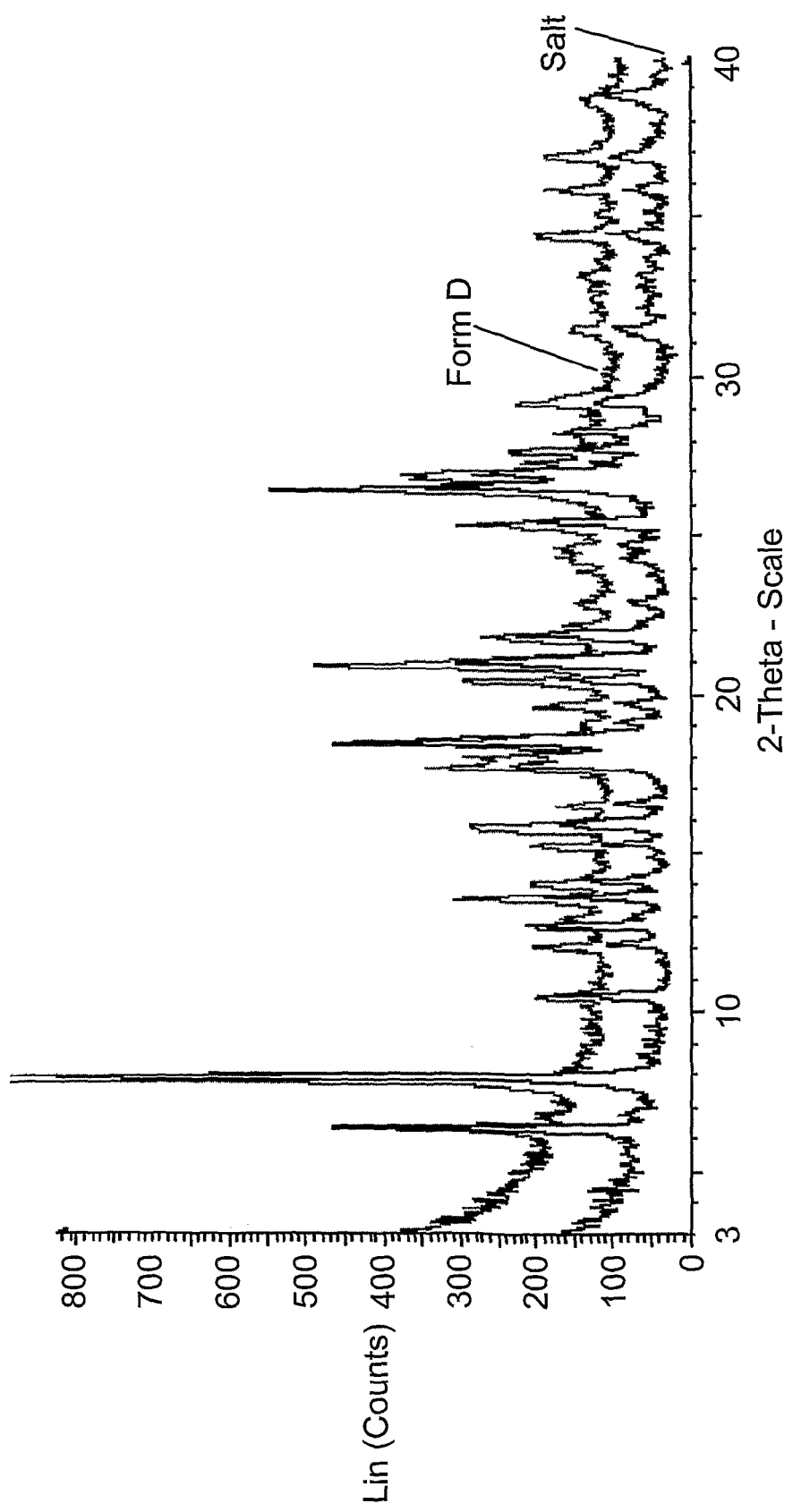
Figure 4D:
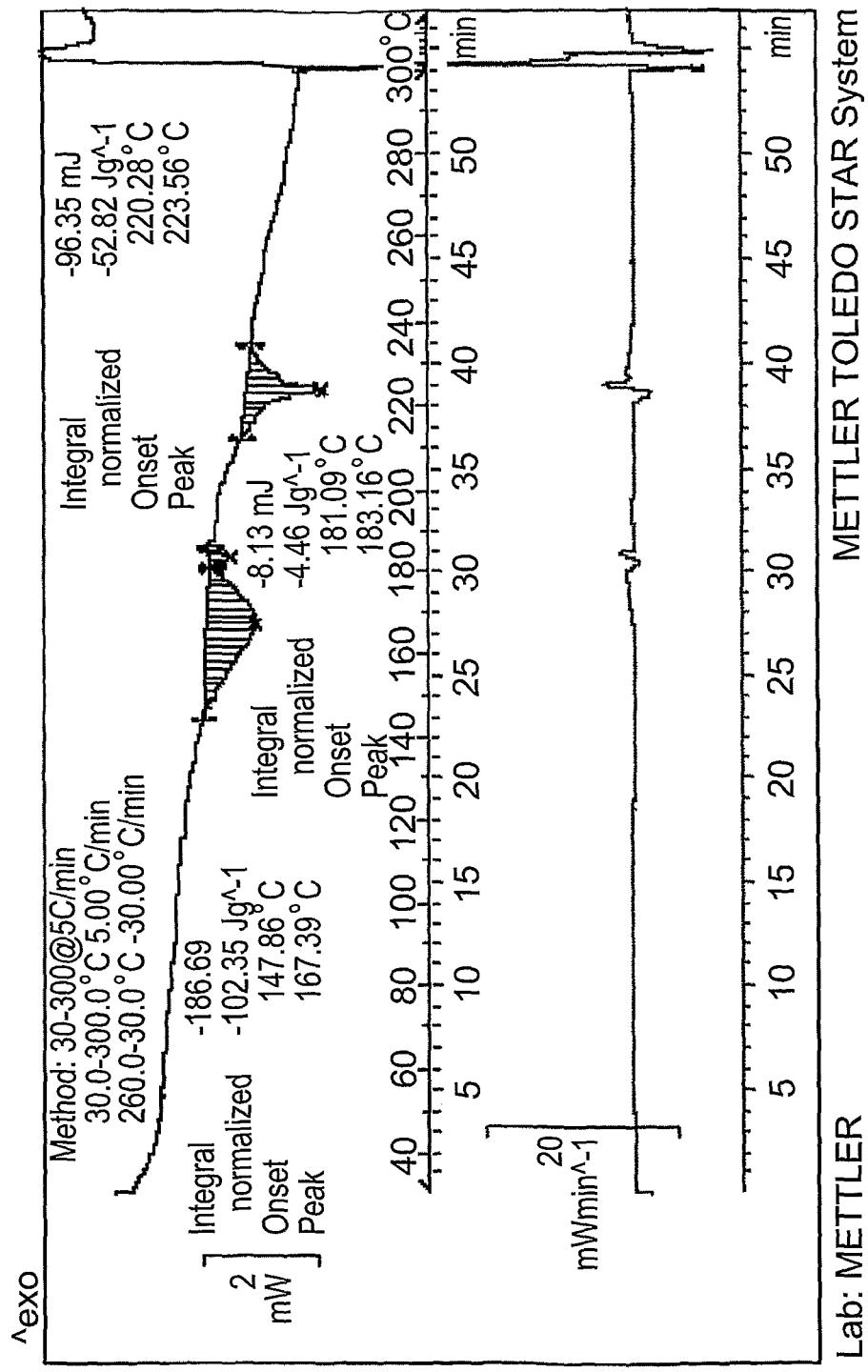
Figure 4E:
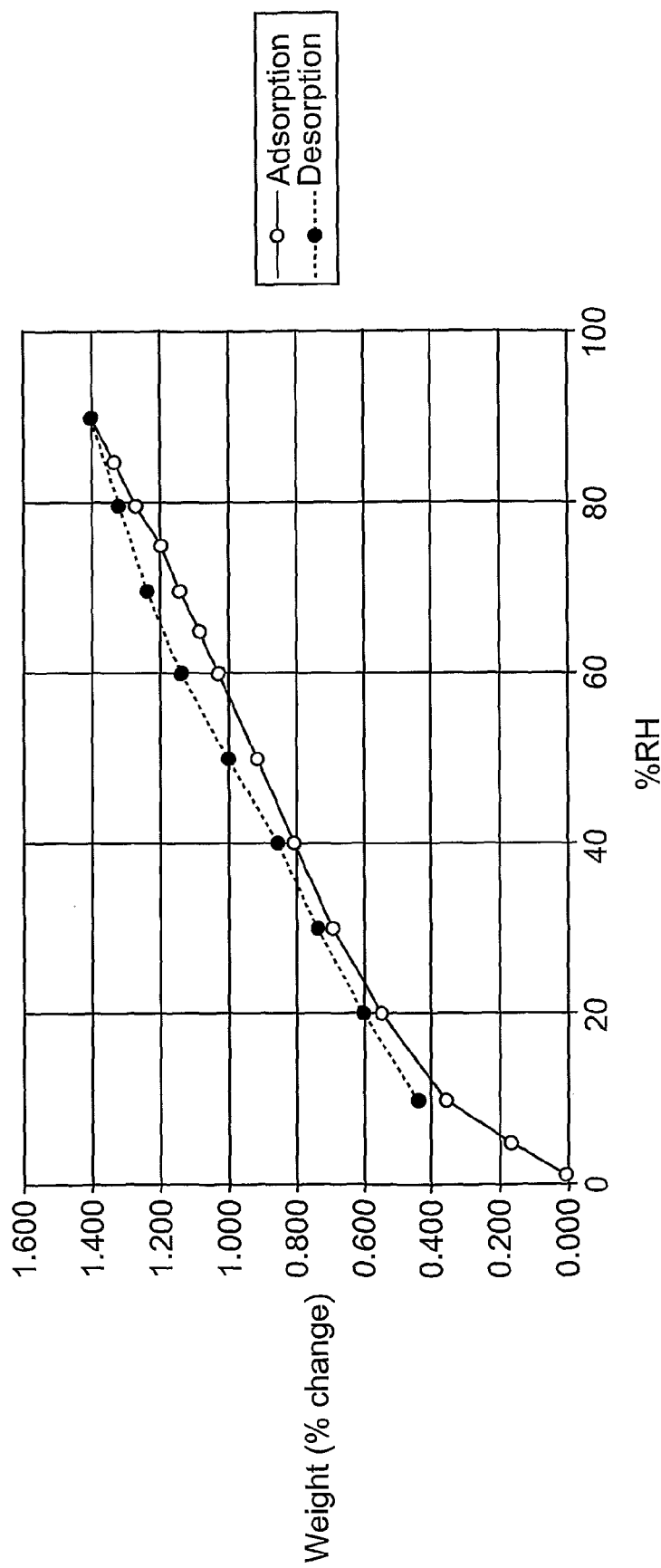

The salts and solvates of the present invention can be characterized by any methods known in the art, including but not limited to elemental analysis, polarized light microscopy, powder X-ray diffraction (PXRD), differential scanning calorimetry (DSC), thermal gravimetric analysis (TGA), thermogravimetric analysis with IR spectroscopy (TGIR), and VTI water vapor adsorption. The mono-besylate, mono-mesylate, and hemihydrate mono-tosylate salts of Formula I provide powder X-ray diffraction spectrums substantially the same as the powder X-ray diffraction spectrums shown in FIGS. 1-3, respectively. However, it is known that a PXRD spectrum may be obtained with a measurement error depending on measurement conditions. In particular, it is generally known that intensities in PXRD spectrum may fluctuate depending on measurement conditions. Therefore, it should be understood that the salts of the present invention are not limited to the crystals that provide PXRD spectra completely identical to the spectra shown in FIGS. 1-3 and that any crystals providing PXRD spectra substantially the same as the aforementioned PXRD spectra fall within the scope of the present invention. Those skilled in the field of PXRD can readily judge the substantial identity of PXRD spectra. Generally, a measurement error of diffraction angle for a usual PXRD is about 5% or less, and such degree of a measurement error should be taken into account as to diffraction angles. Furthermore, it should be understood that intensities may fluctuate depending on experimental conditions.

For example, the salts and solvates of the present invention can be characterized by differential scanning calorimetry (DSC). The besylate salt of Formula I is characterized by a single major endotherm at about 245-255° C. The mesylate salt of Formula I is characterized by a small endotherm at an onset temperature of about 57° C. and a broad endotherm with an onset temperature of about 232° C. The tosylate salt of Formula I is characterized by a single major endotherm with an onset temperature of about 237° C.

The salts and solvates of the present invention can also be characterized by thermogravimetric analysis (TGA). The TGA profile of the besylate salt of Formula I shows less than 0.5% solvent/water loss up to about 255° C. The solvent/water may be tightly bound and not released until melting. The TGIR (thermogravimetric analysis with IR spectroscopy) of the tosylate salt of Formula I shows a total volatile content of 1.4%, consisting of water and ethanol.

The salts and solvates of the present invention can be further characterized by VTI water vapor adsorption to measure hygroscopicity. The besylate salt of Formula I had a weight gain of 0.16% at 90% relative humidity (RH) in this test. The mesylate salt of Formula I had a weight gain of 1.4% at 90% RH, and the tosylate salt of Formula I had a weight gain of 0.6% at 90% RH. Other methods of analysis are described in more detail in the Examples.

A "complex" of the present invention refers generally to any of the salts, solvates or substoichiometric solvates of Formula I described herein.

A "pharmaceutical composition" refers to a mixture of one or more of the complexes described herein with other components, such as physiologically/pharmaceutically acceptable carriers and excipients. The purpose of a pharmaceutical composition is to facilitate administration of a complex to an organism.

As used herein, a "physiologically/pharmaceutically acceptable carrier" refers to a carrier or diluent that does not cause significant irritation to an organism and does not abrogate the biological activity and properties of the administered complex. A "pharmaceutically acceptable excipient" refers to an inert substance added to a pharmaceutical composition to further facilitate administration of a complex. Examples, without limitation, of excipients include calcium carbonate, calcium phosphate, various sugars and types of starch, cellulose derivatives, gelatin, vegetable oils and polyethylene glycols.

By the term "effective amount", or "therapeutically effective amount," as used herein, is meant an amount that when administered to a mammal, preferably a human, mediates a detectable therapeutic response compared to the response detected in the absence of the complex. A therapeutic response, such as, but not limited to, increased overall survival, inhibition of and/or decreased tumor growth (including tumor size stasis), tumor size, metastasis, and the like, can be readily assessed by a plethora of art-recognized methods, including, e.g., such methods as disclosed herein. A "therapeutic effective amount", or "effective amount," is intended to qualify the amount of an agent required to detectably reduce to some extent one or more of the symptoms of a neoplasia disorder, including, but is not limited to: (1) reduction in the number of cancer cells; (2) reduction in tumor size; (3) inhibition (i.e., slowing to some extent, preferably stopping) of cancer cell infiltration into peripheral organs; (4) inhibition (i.e., slowing to some extent, preferably stopping) of tumor metastasis; (5) inhibition, to some extent, of tumor growth; (6) relieving or reducing to some extent one or more of the symptoms associated with the disorder; (7) relieving or reducing the side effects associated with the administration of anticancer agents; and/or (8) increasing, to some extent, the overall survival of a patient relative to that observed for the standard of care for a given tumor type or neoplastic disorder.

A "maintenance effective amount" is intended to qualify the amount of an agent required to detectably maintain the therapeutic benefit achieved during a therapeutic regimen, including, but not limited to (1) inhibiting an increase in the number of cancer cells; (2) inhibiting an increase in tumor size; (3) inhibiting cancer cell infiltration into peripheral organs; (4) inhibiting tumor metastases; (5) relieving or reducing to some extent one or more of the symptoms associated with the disorder; and/or (6) inhibiting a recurrence or onset of one or more of the symptoms associated with the disorder.

Combined with the teachings provided herein, by choosing among the various active complexes and weighing factors such as potency, relative bioavailability, patient body weight, severity of adverse side-effects and preferred mode of administration, an effective prophylactic or therapeutic treatment regimen or maintenance phase can be planned which does not cause substantial toxicity and yet is entirely effective to treat the particular subject. The therapeutic or maintenance effective amount for any particular application can vary depending on such factors as the disease or condition being treated, the severity of the disease or condition, and the health and size of the subject. One of ordinary skill in the art can empirically determine the therapeutic effective amount of a complex of the present invention alone or in combination with one or more additional chemotherapeutic agents, palliative agent, and/or other therapeutic agent without undue experimentation.

As used herein, to "treat" means reducing the frequency with which symptoms of a disease (i.e., tumor growth and/or metastasis, or other effect mediated by the numbers and/or activity of immune cells, and the like) are experienced by a patient. The term includes the administration of a complex of the invention, alone or in combination with one or more additional therapeutic agents to prevent or delay the onset of the symptoms, complications, or biochemical indicia of a disease (e.g., elevation of PSA level in prostate cancer), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

As used herein, to "prevent" means inhibiting the onset or development of symptoms of a disease (i.e., tumor growth and/or metastasis, or other effect mediated by the numbers and/or activity of immune cells, and the like) experienced by a patient. The term includes the administration of a complex of the present invention, alone or in combination with one or more additional therapeutic agents to inhibit or delay the onset of the symptoms, complications, or biochemical indicia of a disease (e.g., elevation of PSA level in prostate cancer).

The therapeutically effective amount or maintenance effective amount of a complex of the present invention can be initially determined from animal models. A therapeutically or maintenance effective dose can also be determined from human data for a complex of the present invention which are known to exhibit similar pharmacological activities. Higher doses may be required for parenteral administration. The applied dose can be adjusted based on the relative bioavailability and potency of the administered complex. Adjusting the dose to achieve maximal efficacy based on the methods described above and other methods as are well-known in the art is well within the capabilities of the ordinarily skilled artisan.

Except when noted, the terms "patient" or "subject" are used interchangeably and refer to mammals such as human patients and non-human primates, as well as veterinary subjects such as rabbits, rats, and mice, and other animals. Preferably, patient refers to a human.

This invention also relates to a method for the treatment of abnormal cell growth in a mammal, including a human, comprising administering to said mammal an amount of a complex of the formula 1, as defined above that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises administering to a mammal an amount of a complex of formula 1 that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

This invention also relates to a method for the treatment of abnormal cell growth in a mammal which comprises administering to said mammal an amount of a complex of formula 1 that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens. A non-limiting list of suitable therapeutic agents that may be used in combination with the complexes of the present invention are provided in U.S. Ser. No. 11/127,809, the disclosure of which is hereby incorporated herein by reference.

This invention also relates to a pharmaceutical composition for the treatment of abnormal cell growth in a mammal, including a human, comprising an amount of a complex of the formula 1, as defined above, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

This invention also relates to a method for the treatment of a disorder associated with angiogenesis in a mammal, including a human, comprising administering to said mammal an amount of a complex of the formula 1, as defined above, or a pharmaceutically acceptable salt, solvate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections, including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise administering an amount of a complex of formula 1, or a pharmaceutically acceptable salt, solvate or prodrug thereof, in combination with an amount of one or more substances selected from anti-angiogenesis agents, signal transduction inhibitors, and antiproliferative agents, which amounts are together effective in treating said abnormal cell growth.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The complexes of the present invention are potent inhibitors of the FAK protein tyrosine kinases, and thus are all adapted to therapeutic use as antiproliferative agents (e.g., anticancer), antitumor (e.g., effective against solid tumors), antiangiogenesis (e.g., stop or prevent proliferationation of blood vessels) in mammals, particularly in humans. In particular, the complexes of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a complex of the present invention may possess activity against a range of leukemias and lymphoid malignancies.

In a more preferred embodiment cancer is a solid tumor, such as, but not limited to, breast, lung, colon, brain, prostate, stomach, pancreatic, ovarian, skin (melanoma), endocrine, uterine, testicular, and bladder.

The complexes of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the complexes of the present invention may have therapeutic utility in inflammatory, angiogenic and immunologic disorders involving both identified and as yet unidentified tyrosine kinases that are inhibited by the complexes of the present invention.

A particular aspect of this invention is directed to methods for treating or preventing a condition that presents with low bone mass in a mammal (including a human being) which comprise administering to a mammal in need of such treatment a condition that presents with low bone mass treating amount of a Formula I complex.

This invention is particularly directed to such methods wherein the condition that presents with low bone mass is osteoporosis, frailty, an osteoporotic fracture, a bone defect, childhood idiopathic bone loss, alveolar bone loss, mandibular bone loss, bone fracture, osteotomy, periodontitis or prosthetic ingrowth.

A particular aspect of this invention is directed to methods for treating osteoporosis in a mammal (including a human being) which comprise administering to a mammal in need of such treatment an osteoporosis treating amount of a Formula I complex.

Another aspect of this invention is directed to methods for treating a bone fracture or an osteoporotic fracture in a mammal which comprise administering to a mammal in need of such treatment a bone fracture treating or an osteoporotic fracture treating amount of a Formula I complex.

The term "osteoporosis" includes primary osteoporosis, such as senile, postmenopausal and juvenile osteoporosis, as well as secondary osteoporosis, such as osteoporosis due to hyperthyroidism or Cushing syndrome (due to corticosteroid use), acromegaly, hypogonadism, dysosteogenesis and hypophosphatasemia.

The complexes of the invention may be administered in a dosage regimen which can be adjusted to provide the optimum desired response. For example, a single bolus can be administered, several divided doses can be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active complex calculated to produce the desired therapeutic effect in association with the required pharmaceutical carrier. The specification for the dosage unit forms of the invention are dictated by and directly dependent on (a) the unique characteristics of the chemotherapeutic agent and the particular therapeutic or prophylactic effect to be achieved, and (b) the limitations inherent in the art of complexing such an active complex for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient can also be determined, as can the temporal requirements for administering each agent to provide a detectable therapeutic benefit to the patient. Accordingly, while certain dose and administration regimens are exemplified herein, these examples in no way limit the dose and administration regimen that can be provided to a patient in practicing the present invention. Further, one skilled in the art would understand, once armed with the teachings provided herein, that a therapeutic benefit, such as, but not limited to, detectable decrease in tumor size and/or metastasis, and increased time to recurrence, among many other parameters, can be assessed by a wide variety of methods known in the art for assessing the efficacy of treatment of cancer, and these methods are encompassed herein, as well as methods to be developed in the future.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regiments for administration of the chemotherapeutic agent are well-known in the relevant art and would be understood to be encompassed by the skilled artisan once provided the teachings disclosed herein.

The complex of the present invention may be administered in one of two dosage types referred to herein as a therapeutic dose and a maintenance dose. Therapeutic dose refers to the dose of the complex administered to a patient during a cycle of therapy in which one or more additional chemotherapeutic agents are administered during the cycle of therapy. For example, if a patient begins 6 cycles of chemotherapy (referred to as a "treatment regimen"), in which one cycle comprises several weekly administrations of the complex, chemotherapeutic agents, or combinations thereof, the doses of the complex administered to the patient in the course of this therapeutic regimen is referred to as a therapeutic dose. In contrast, maintenance dose refers to the dose of the complex administered to a patient after the completion of a therapeutic regimen. The maintenance dose is administered during a "maintenance phase" which is separate in time and distinct in objectives from the treatment regimen.

The therapeutic dose and the maintenance dose may be the same or different at any point in the therapeutic continuum. For example, the patient's initial maintenance dose may be the same as the therapeutic dose, but after a certain interval of time and depending on a variety of factors, including but not limited to stage of disease before and after the completion of a therapeutic regimen, overall well-being of the patient after the completion of a therapeutic regimen, concomitant disease conditions, etc., the maintenance dose may be increased or decreased relative to the therapeutic dose.

Administration of the complexes of the present invention can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the complex administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The complex may be administered substantially simultaneously or sequentially with chemotherapeutic agent(s) of the invention during the therapeutic regimen or maintenance phase. Regardless of the stage of the treatment continuum, when administration is simultaneous, the complex and the chemotherapeutic agent may be in the same or separate formulations although they are administered at the same time. The term "substantially simultaneously" means that the complexes are administered within minutes of each other (e.g., within 10 minutes of each other) and intends to embrace joint administration as well as consecutive administration, but if the administration is consecutive it is separated in time for only a short period (e.g., the time it would take a medical practitioner to administer two complexes separately). As used herein, concurrent administration and substantially simultaneous administration are used interchangeably. Sequential administration refers to temporally separated administration of the complex and the chemotherapeutic agent. The separation in time between the administration of these complexes are deliberately longer than the time it takes to administer two medicaments separately, one after the other, without intended delay. Co-administration thus encompasses any temporal combination of administration of the chemotherapeutic agent and the complex such that administration of the two mediates a therapeutic benefit to the patient that is detectably greater than administration of either agent in the absence of the other.

The complex may be administered before, concurrently with, or after (or any combination thereof) administration of the chemotherapeutic agent, and vice versa. The complex may be administered daily (including one or more administrations per day), every other day, every three days, every four days, every five days, every six days, or every week, every month, every two months, every three months, every four months, every five months, every six months, or every year. The chemotherapeutic agent may be administered daily, every other day, every three days, every four days, every five days, every six days, every week, every two weeks, monthly, or every twenty days, every 25 days, every 28 days, every 30 days, every 40 days, every 50 days, every two months, every 70 days, every 80 days, every three months, every six months or yearly. A single dose or multiples doses of the chemotherapeutic agent may be administered. Alternatively, at least one dose, or at least three, six or 12 doses may be administered.

The invention encompasses the preparation and use of pharmaceutical compositions comprising a human chemotherapeutic agent of the invention as an active ingredient in combination with and without the complex. Such a pharmaceutical composition may consist of each active ingredient alone, as a combination of at least one active ingredient (e.g., an effective dose of a chemotherapeutic agent, an effective dose of the complex) in a form suitable for administration to a subject, or the pharmaceutical composition may comprise the active ingredient and one or more pharmaceutically acceptable carriers, one or more additional (active and/or inactive) ingredients, or some combination of these.

The complex can be administered by a variety of methods known in the art, including, without limitation, oral, parenteral, mucosal, by-inhalation, topical, buccal, nasal, and rectal. For many therapeutic applications, the preferred route/mode of administration is subcutaneous, intramuscular, intravenous or infusion. Non-needle injection may be employed, if desired. As is appreciated by the skilled artisan, the route and/or mode of administration will vary depending upon the desired results.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient (or complex) is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics, anti-diarrheals, chemotherapeutic agents, cytokines, and the like. Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations as discussed below. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

A composition of the present invention can be administered by a variety of methods known in the art. The route and/or mode of administration vary depending upon the desired results. The compositions can be prepared with carriers that protect the complex against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are described by e.g., Sustained and Controlled Release Drug Delivery Systems, J. R. Robinson, ed., Marcel Dekker, Inc., New York, (1978). Pharmaceutical compositions are preferably manufactured under GMP conditions.

The chemotherapeutic agent/the complex active ingredient combination of the invention can be administered to an animal, preferably a human. While the precise dosage administered of each active ingredient will vary depending upon any number of factors, including but not limited to, the type of animal and type of disease state being treated, the age of the animal and the route(s) of administration.

EXAMPLES

Example 1

Preparation and Analysis of Free Base and Monobesylate Salt of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide (Step 1) Trifluoromethyluracil (5.00 kg, 1 eq.), phosphorous oxychloride (21.50 kg, 5 eq.), and an 85 wt. % solution of phosphoric acid in water (320 g, 0.1 eq.) were charged to a reactor that was boiled out with ethanol and had a caustic scrubber attached. N,N-diisopropylethylamine (3.62 kg, 1 eq.) was separated into five charges, the first four being 1 liter and the fifth 0.9 liters and added at a rate keeping the temperature of the reaction mixture between 20 and 40° C. The reaction mixture was heated to 100° C. over 2 hours and held for 20 hours. After cooling to 20-30° C., the reaction mixture was transferred into a stirred 1:1 solution of hexanes/water (10 L/kg:10 L/kg) at a rate where the temperature did not exceed 50° C. and the time of transfer was at least 3 hours. The hexanes layer was washed twice with water (5 L/kg) and dried with magnesium sulfate (1.00 kg) followed by a filtration and rinse with hexanes (1 L/kg). Hexanes were removed by distillation at atmospheric pressure with a final distillate temperature of 75° C. and pot temperature of 100° C. GC headspace indicated 2.1% hexanes remained in the final product.

(Step 2) T-butyl alcohol (3 L/kg) and zinc dibromide (5.07 kg) were charged to the reactor then stirred for 10 minutes. 5-Aminooxindole (3.00 kg) and dichloroethane (3 L/kg) were then added followed by stirring 30 minutes. The product from Step 1 was added then the triethylamine was added over 30 minutes keeping the temperature below 35° C., and the reaction mixture was stirred overnight. Methanol (13.5 L) was added to the reaction mixture. The reaction mixture was then filtered through two Buchner funnels over several hours, filtration was aided by constantly moving the filter cake. The filter cakes were rinsed with methanol (6.4 L). The reactor was charged with methanol (15 L) and the wet cake was returned to the reactor and stirred for 1 hour, filtered over two Buchner funnels and washed with methanol (2.5 L). Trituration and filtration were repeated and the product was dried in the vacuum dried at 33° C. for 12 hours. GC headspace showed 0.1% methanol remained in the product.

(Step 3) To the reactor, isopropyl alcohol (3 L/kg), toluene (3 L./kg), the product of step 2 (3.61 kg), and N-(3-Aminomethyl-2-pyridyl)-N-methylmethanesulfonamide diacetate (4.79 kg, 1.3 eq.) were charged. N,N-diisopropylamine was then added at rate to keep the temperature between 10-25° C. The reactor was heated to reflux, 85-90° C., for 5 hours then cooled to 20-30° C. and held for 1.4 hours. The reaction mixture was filtered through a Nutche filter to isolate the solid and rinsed with isopropyl alcohol (10.8 L). Acetonitrile (40.0 L) was added to the reactor followed by the isolated solid then stirred for 12 hours. The slurry was transferred to a Nutche filter for isolation. The filter cake was washed with acetonitrile (18.1 L) then placed in the dryer for 12 hrs at 40° C. GC headspace results were 0.48% acetonitrile. HPLC results showed 98.49% purity with one major impurity at 0.97%. Yield was 68.3%.

(Step 4) To a Naljug, benzenesulfonic acid (1.8 kg, 1.5 eq.) and water (2 L) were added and agitated until the solution was homogeneous. The solution was then added to the reactor under speck free conditions. The product of step 3, the free base of Formula I (3.8 kg) was charged to a separate reactor followed by ethanol/water (20 gal/15 gal), the heated to 70° C. The hot slurry was transferred to the reactor containing the salt solution under speck free conditions. The reactor was cooled to 20-30° C. over 2 hrs then held between 20-30° C. for 12 hours. No solids were collected upon the first filtration. The solution was returned to the reactor under speck free conditions and the reactor cooled to 10-20° C. Material rapidly crystallized out of solution and was granulated for 12 hours. The slurry was filtered through a Nutche filter and the solids were isolated and dried for 24 hours at 20-30° C. The material was milled using the Bantam Mill. The final amount isolated was 4.02 kg, overall yield 82%.

The monobesylate salt of Formula I (m. wt. 665.67), Form A, was a white crystalline solid with irregularly-shaped particle morphology ranging from approximately 5-50 mm in diameter. This anhydrous form melted (DSC, Tonset) at 254° C. with decomposition. This material was non-hygroscopic and chemically and physically stable in the solid-state through three weeks exposure to 70° C./75% RH exposure.

In solution, the monobesylate salt of Formula I existed as a weak base, with a pKa of 4.58. This moderately lipophilic molecule (c Log P=2.2) was found to possess low aqueous solubility above pH 5 of about 5 mgA/ml. Solubility increased in acidic media, with a solubility of 1 mgA/ml observed in pH 2 buffer. The solubility in unbuffered water (pH 2.65) was 369 mgA/ml. Solubility determined in several common organic solvents, such as ethanol and acetone, was about 200 mgA/ml. The following table summarizes the physical and chemical properties of the monobesylate salt of Formula I:

| | |
|---|---|
| Melting onset (DSC) | 254° C. |
| % Volatiles (TGA, 30-200 C.) | 0% |
| Hygroscopic moisture gain at 90% RH (VTI) | 0.09% |
| Particle Shape/Size | Irregular/5-50 micrometer diameter |
| pKa | 4.58, weak base |
| Unbuffered water solubility (pH 2.65) | 369 ugA/ml |
| Aqueous buffer pH 7 solubility | 4 ugA/ml |
| Aqueous buffer pH 1.4 solubility | 1162 ugA/ml |
| Ethanol/Acetone solubility | 260/206 ugA/ml |
| cLog P | 2.21 |
| Solid-state stability, 3 weeks at 70 C./75% RH | >99.9% (purity by HPLC area % relative to room temperature control) |

This monobesylate salt of Formula I appeared as fine crystalline particles of moderate to high birefringence with irregularly-shaped morphology. The size of the particles ranged from approximately 5 mm to 50 mm in diameter, with some aggregates up to about 200 mm in diameter. The material was tested using DSC at a heating rate of five degrees/minute, FIG. 1(b). A sharp melting endotherm with onset temperature of 254° C. was observed. Minor front tailing for the endotherm was also noted. The material was tested by TGA at a heating rate of five degrees/minute, FIG. 1(c). No loss in weight was observed up to the melting onset temperature (~250)° C. Detailed analysis revealed the presence of 0.3% water and 0.7% ethanol. These solvents were thus likely entrained by the crystal and were not released until melting. Melting with concurrent decomposition was suggested by weight loss above 260° C. The dynamic moisture sorption was evaluated using a flow-through VTI apparatus at 25° C.

The sample was initially dried at ~2% RH for maximum of two hours, followed by a moisture adsorption ramp from 10% RH to 90%, then a desorption ramp back down to 10% RH. Initial drying removed 0.08% by weight, followed by a maximum moisture gain of 0.09% at 90% RH. Thus, this complex was non-hygroscopic.

Example 2

Preparation and Analysis of Monobesylate Salt of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide A solution of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide (200 mg, 0.39 mmol) in ethanol (8 mL) was heated on a steam bath until completely dissolved. Water (8 mL, ~40° C.) was added to the solution and cooled to room temperature. Phenylsulfonic acid (67 mg, 0.41 mmol) in ethanol (1 mL) was added to the solution and stirred for 5 days. The solution was filtered and dried to provide the title complex as a white solid (148 mg, 57%). MP 255° C. (DSC); Hygroscopicity: 0.16% (by weight) at 90% relative humidity at ambient temperature (RH); Characteristic X-ray powder diffraction peaks (2-theta, [% relative intensity]): 15.891 [48.1], 16.197 [48.5], 18.085 [47.3], 18.445 [100], 20.194 [44.2], 21.18 [37.9], 22.655 [74.5], 23.015 [99.7], 23.676 [45.9], 26.55 [45.2] and 27.736 [45.9]; Combustion analysis (theoretical/experimental) of monobesylate salt containing 0.67% $H_2O$: carbon (48.39/48.25), hydrogen (3.99/3.76), nitrogen (14.63/14.51), fluorine (8.50/8.48), sulfur (9.57/9.92).

Example 3

Preparation and Analysis of Monomesylate Salt of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide A solution of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide (250 mg, 0.49 mmol) in THF (7.5 mL) was heated on a steam bath until completely dissolved. THF (2.5 mL) was added to the solution and cooled to room temperature. Methanesulfonic acid (50 mg, 0.57 mmol) was added to the solution and stirred for 24 h. THF was added (5 mL) and the solution was filtered and dried to provide the title complex as a white solid (300 mg, 72%). MP 232° C. (DSC); Hygroscopicity: 1.4% (by weight) at 90% relative humidity at ambient temperature (RH); Characteristic X-ray powder diffraction peaks (2-theta, [% relative intensity]): 7.95 [70.5], 11.495 [48.3], 11.852 [48.8], 13.814 [37.4], 17.505 [100], 18.038 [47.3], 18.81 [79.3], 19.313 [73.6], 19.627 [72.2], 20.89 [66.8], 22.397 [59.1], 23.169 [44.2] and 27.787 [46.3]; Combustion analysis (theoretical/experimental) of monomesylate salt containing 1% THF: carbon (44.01/43.74), hydrogen (4.08/4.05), nitrogen (16.08/15.60), fluorine (9.35/9.19), sulfur (10.52/10.82).

The sample of monomesylate salt of Formula I consisted of fine birefringent rods and flakes of less than ten micron. Particles showed at least two different extinction patterns, suggesting the presence of different polymorphic forms. The monomesylate salt of Formula I was crystalline with minor disorder by PXRD as shown in FIG. 2. The thermal profile of this sample was obtained by heating from 30-300 C at 5 C/min. The sample tested showed a very small endotherm with an onset temperature of 57° C. and a broad endotherm with overlapping thermal events, with an onset temperature at 232° C. The thermal behavior of this sample was visually observed by light microscopy while heating from 30-300° C. at 5° C./min. The monomesylate showed particle motion from about 170° C., which might relate to release of solvent. Gradual melting was observed beginning at about 180° C., with the entire sample melted by 235° C. These observations suggested that the broad melting range may be a result of a mixture of forms and/or several competing thermal processes including polymorph conversion occurring during heating.

The sample was tested in flow-through VTI with relative humidity ramp from 0 to 90%, then a desorption ramp back down to 10%1 RH at 25 C. This sample had a weight gain of 1.4% at 90% RH. Thus, this material can be considered kinetically non-hygroscopic. The monomesylate was analyzed for elemental composition of carbon, hydrogen, nitrogen, fluorine and sulfur. The results from analysis met the stoichiometry of a mono-mesylate salt containing 1% THF.

Example 4

Preparation and Analysis of Tosylate Salt of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide A solution of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide (5.4 g, 10.6 mmol) in ethanol (250 mL) was heated on a steam bath until completely dissolved. The solution was cooled to room temperature and p-toluenesulfonic acid (2.2 g, 11.2 mmol) in ethanol (30 mL) was added to the solution and stirred for 12 h. The solution was filtered and dried to provide the title complex as a white solid (5.6 g, 78%). MP 237° C. (DSC); Hygroscopicity: 0.6% (by weight) at 90% relative humidity at ambient temperature (RH); Characteristic X-ray powder diffraction peaks (2-theta, [% relative intensity]): 4.4 [37.4], 6.425 [81.5], 7.537 [48.1], 12.925 [42.1], 15.132 [79.1], 17.582 [47.4], 18.009 [51.1], 18.531 [100], 19.493 [52.4], 19.888 [91], 21.647 [56.4], 21.987 [70.1], 25.305 [79.3], 25.913 [79.3] and 27.787 [46.3]; Combustion analysis (theoretical/experimental) of monotosylate salt as the hemihydrate: carbon (48.83/48.83), hydrogen (4.24/3.96), nitrogen (14.24/14.02), fluorine (8.28/8.32), sulfur (9.31/9.42).

The hemihydrate tosylate salt of Formula I consisted of fine birefringent aggregated needles and lathes. This sample was crystalline by PXRD. The thermal profile of this sample was obtained by heating from 30-300 C at 5 C/min. The sample showed a single major endotherm with an onset temperature at 237° C., which is higher than Form A with a melting onset of 216° C. The volatile content of this sample was obtained by heating from 30-225 C at 5 C/min. The total volatile content was 1.4%, and consisted of water and ethanol by IR. The sample was tested in flow-through VTI with relative humidity ramp from 0 to 90% at 25 C. This sample had a weight gain of 0.6% at 90% RH. It is kinetically non-hygroscopic.

Example 5

Preparation and Analysis of HCl Salt of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide A solution of N-Methyl-N-(3-{[2-(2-oxo-2,3-dihydro-1H-indol-5-ylamino)-5-trifluoromethyl-pyrimidin-4-ylamino]- methyl}-pyridin-2-yl)-methanesulfonamide (100 mg, 0.20 mmol) in ethanol (5 mL) was heated on a steam bath until completely dissolved. Ethanol (1 mL) was added to the solution and cooled to room temperature. Hydrochloric acid (4M in dioxane, 0.054 mL, 0.22 mmol) was added to the solution and stirred for 7 days. The reaction mixture was filtered and dried to provide the title complex as a white solid. MP 124° C. (DSC); Hygroscopicity: 2.7% (by weight) at 90% relative humidity at ambient temperature (RH); Characteristic X-ray powder diffraction peaks (2-theta, [% relative intensity]): 3.632 [42.9], 4.889 [36], 5.824 [54.8], 7.998 [92.7], 11.458 [60.7], 12.725 [46.5], 14.911 [68.3], 15.528 [61.1], 18.545 [83.2], 19.147 [67.3], 20.747 [61.4], 21.04 [51.2], 22.696 [40.3], 23.293 [45.5], 25.198 [39.9], 26.05 [100] and 26.32 [83.2]; Combustion analysis (theoretical/experimental) of mono HCl salt as the anhydrate: carbon (46.37/46.39), hydrogen (3.89/3.88), nitrogen (18.03/17.83), fluorine (10.48/10.69), sulfur (5.89/5.88).

Example 6

Preparation and Analysis of HCl Salt of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide A solution of N-Methyl-N-(3-{[2-(2-oxo-2,3-dihydro-1H-indol-5-ylamino)-5-trifluoromethyl-pyrimidin-4-ylamino]-methyl}-pyridin-2-yl)-methanesulfonamide (250 mg, 0.49 mmol) in THF (10 mL) was heated on a steam bath until completely dissolved. The solution was cooled to room temperature and hydrochloric acid (2M in ethyl ether, 0.27 mL, 0.52 mmol) was added to the solution and stirred for 24 h. The reaction mixture was filtered and dried to provide the title complex as a white solid (250 mg, 94%). MP 220° C. (DSC); Hygroscopicity: 1.4% (by weight) at 90% relative humidity at ambient temperature (RH); Characteristic X-ray powder diffraction peaks (2-theta, [% relative intensity]): 6.321 [56.4], 7.904 [100], 18.498 [53.3], 21.02 [36.7] and 26.558 [41.3]; Combustion analysis (theoretical/experimental) of mono HCl salt containing 9% THF: carbon (48.2/47.7), hydrogen (4.55/4.45), nitrogen (16.4/15.8), fluorine (9.53/9.24), sulfur (5.36/6.09), chlorine (5.93/5.70).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated herein by reference in their entireties.

The invention claimed is:

1. A pharmaceutically acceptable besylate, mesylate, or tosylate salt of N-[3-[[[2-[(2,3-dihydro-2-oxo-1H-indol-5-yl)amino]-5-(trifluoromethyl)-4-pyrimidinyl]amino]methyl]-2-pyridinyl]-N-methylmethanesulfonamide.

2. The salt of the compound of claim 1, wherein said salt is a besylate salt.

3. The salt of the compound of claim 1, wherein said salt is a mesylate salt.

4. The salt of the compound of claim 1, wherein said salt is a tosylate salt.

5. A pharmaceutical composition comprising a salt according to claim 1 and a pharmaceutically acceptable carrier or diluent.

* * * * *